US012800575B2

(12) United States Patent
Katzlinger et al.

(10) Patent No.: US 12,800,575 B2
(45) **Date of Patent: *Nov. 17, 2026**

(54) REAL TIME WESTERN BLOT ASSAYS UTILIZING FLUORESCENCE RESONANCE ENERGY TRANSFER (FRET)

(71) Applicant: Molecular Devices (Austria) GmbH, Wals (AT)

(72) Inventors: Michael Katzlinger, Eugendorf (AT); Kamil Önder, Salzburg (AT)

(73) Assignee: Molecular Devices (Austria) GmbH (AT)

( * ) Notice: Subject to any disclaimer, the term of this patent is extended or adjusted under 35 U.S.C. 154(b) by 601 days.

This patent is subject to a terminal disclaimer.

(21) Appl. No.: 18/166,971

(22) Filed: Feb. 9, 2023

(65) Prior Publication Data

US 2023/0236177 A1 Jul. 27, 2023

Related U.S. Application Data

(63) Continuation of application No. 16/163,136, filed on Oct. 17, 2018, now Pat. No. 11,604,186.

(51) Int. Cl.
*G01N 33/542* (2006.01)
*G01N 21/64* (2006.01)

(52) U.S. Cl.
CPC ....... *G01N 33/542* (2013.01); *G01N 21/6428* (2013.01); *G01N 21/645* (2013.01); *G01N 2021/6439* (2013.01); *G01N 2474/10* (2021.08)

(58) Field of Classification Search
None
See application file for complete search history.

(56) References Cited

U.S. PATENT DOCUMENTS

| | | | |
|---|---|---|---|
| 6,287,781 | B1 | 9/2001 | Lee et al. |
| 6,844,166 | B1 | 1/2005 | Wolf |
| 7,666,645 | B2 | 2/2010 | Wang |
| 11,604,186 | B2 | 3/2023 | Katzlinger et al. |
| 2002/0042083 | A1 | 4/2002 | Issakani et al. |
| 2009/0227043 | A1 | 9/2009 | Huang |
| 2012/0202191 | A1 | 8/2012 | McGiven |
| 2012/0258870 | A1 | 10/2012 | Schwartz et al. |
| 2013/0060105 | A1 | 3/2013 | Shah et al. |
| 2013/0177930 | A1 | 7/2013 | Zhang |
| 2014/0038222 | A1 | 2/2014 | Alt et al. |
| 2014/0308657 | A1 | 10/2014 | Lu et al. |
| 2016/0299076 | A1 | 10/2016 | Katzlinger |
| 2016/0299079 | A1 | 10/2016 | Schramm et al. |

FOREIGN PATENT DOCUMENTS

| | | | |
|---|---|---|---|
| CA | 2 353 920 | A1 | 7/2000 |
| CN | 1396265 | A | 2/2003 |
| CN | 101321878 | A | 12/2008 |
| CN | 101868728 | A | 10/2010 |
| CN | 102918387 | A | 2/2013 |
| JP | 2008-167678 | A | 7/2008 |
| JP | 2018-518657 | A | 7/2008 |
| JP | 2021-521108 | | 8/2021 |
| WO | 02/066982 | | 8/2002 |
| WO | 2004/042404 | | 5/2004 |
| WO | 2006/004936 | A2 | 1/2006 |
| WO | 2008065540 | | 6/2008 |
| WO | 2009/105583 | A1 | 8/2009 |
| WO | 2010051473 | A2 | 5/2010 |
| WO | 2018/087093 | A1 | 5/2018 |

OTHER PUBLICATIONS

Kurien et al., Western Blotting: An Introduction, Methods Mol. Biol., 1312, (2015), p. 17-30. (Year: 2015).*
Amersham Pharmacia Biotech (technical manual), Fluorescence Imaging, Principles and Methods, 2000 (144 pages), < https://www.bu.edu/pic/files/2010/10/Fluor-ImagingPrinciples.pdf> (Year: 2000).
Application Note: Detection and quantitation of protein with ScanLater Western Blot Detection System, Copyright 2016 Molecular Devices, LLC 2/16.
Busch et al., An In Vivo Spectral Multiplexing Approach for the Cooperative Imaging of Different Disease-Related Biomarkers with Near-Infrared Fluorescent Forster Resonance Energy Transfer Probes, The Journal of Nuclear Medicine, 53(4), (2012), p. 638-646. (Year: 2012).
Dennis. Allison M. et al., Quantum Dot—Fluorescent Protein Pairs as Novel Fluorescence Resonance Energy Transfer Probes, Georgia Institute of Technology and Emory University, Nano Letters 2008, vol. 8, No. 5 1439-1445.
Ergin et al., Time-Resolved Fluorescence Resonance Energy Transfer [TR-FRET] Assays for Biochemical Processes, Current Pharmaceutical Biotechnology, 17(14), (2016), p. 1222-1230 (Year: 2016).
Fassnacht et al., AKT Is Highly Phosphorylated in Pheochromocytomas But Not in Benign Adrenocortical Tumors, The journal of clinical endocrinology & Metabolism, 90(7), (2005), p. 4366-4370. (Year: 2005).
Fret Substrates, Sachem, Pioneering Partner for Peptides, 2004068 published by Global Marekting, Bachem Group, May 2017.
Held, Paul, An Introduction to Fluorescence Resonance Energy Transfer (FRET) Technology and its Application in Bioscience, BioTek Instruments, Inc., Winoosky, VT BioTek White Paper Copyright 2012, 6 pgs.
Horton, Robert A. et al., Multiplexing Terbium- and Europium-Based TR-FRET Readouts to Increase Kinase Assay Capacity, Journal of Biomolecular Screening 15(8); 2010.
International Search Report and Written Opinion for Application No. PCT/IB2019/058864 mailed Mar. 11, 2020 (11 pages).

(Continued)

*Primary Examiner* — Ellen J Marcsisin
(74) *Attorney, Agent, or Firm* — Merchant & Gould P.C.

(57) ABSTRACT

The present invention generally relates to Western Blot assays in which measurements of target proteins are performed in real time based on fluorescence resonance energy transfer FRET) events.

28 Claims, 11 Drawing Sheets

(56) References Cited

OTHER PUBLICATIONS

Kiaotian Cui et al., "TR-FRET Assays of Huntingtin Protein Fragments Reveal Temperature and PolyQ Length-Dependent Conformational Changes", Scientific Reports, vol. 4, 2014, pp. 1-8.
Mechaly et al., A novel homogeneous immunoassay for anthrax detection based on the AlphaLISA method: detection of B. anthracis spores and protective antigen (PA) in complex samples, Anal. Bioanal. Chem., 405, (2013), p. 3965-3972. (Year: 2013).
Reverdatto et al., Peptide Aptamers: Development and Applications, Curr. Top. Med. Chem., 15(12), (2015), p. 1082-1101. (Year: 2015).
ScanLater Western Blot Detection System, Enabling the SpectraMax i3/i3x and Paradigm microplate readers, Copyright 2016 Molecular Devices, LLC 2/16.
Szöllősi et al., Application of Fluoresence Resonance Energy Transfer in the Clinical Laboratory: Routine and Research, Cytometry (Communications in Clinical Cytometry), 34, (1998), p. 159-179 (Year: 1998).
Busch, Corinna, et al., "An in vivo spectral multiplexing approach for the cooperative imaging of different disease-related biomarkers with near-infrared fluorescent Forster resonance energy transfer probes", Journal of Nuclear Medicine, vol. 53, No. 4, Mar. 9, 2012, pp. 638-646.
CF Wu et al., "A green fluorescent protein fusion strategy for monitoring the expression, cellular location, and separation of biologically active organophosphorus hydrolase", Applied Microbiology and Biotechnology, 2000, 54; pp. 78-83.
Lei, Guo, et al., "New advances in protein-protein interaction research techniques", Journal of Tianjin Medical University, vol. 21, Issue 6, Nov. 20, 2015, pp. 542-544.
Lei, Liu et al., "Study of Intracellular Calcium-Induced Apoptotic Signaling Pathways Using Fluorescence Resonance Energy Transfer Technology", Progress in Biochemistry and Biophysics, 36(9), Sep. 15, 2009, pp. 1172-1180. (with English translation entitled "Using FRET Technique to Investigate the Apoptotic Mechanism Induced by Cisplatin in Living Cells".).
Longsheng, Wang et al., "Real-time Detection of Cellular CAMP Levels Using Fluorescence Resonance Energy Transfer (FRET)", Acta Universitatis Medicinalis Anhui, vol. 52, No. 11, Sept. 8, 2017, pp. 1726-1730. (with English translation).
PCT International Preliminary Report on Patentability in Application PCT/IB2019/058864 mailed Apr. 29, 2021, 8 pages.
Riuttamaki, Terhi, "Upconverting Phosphor Technology: Exceptional Photoluminescent Properties Light Up Homogenous Bioanalytical Assays", University of Turku Publications (2011), 93 pages.
Ye Yousheng et al., "Determination of paracetamol by electrochemiluminescence based on molecularly imprinted membrane resonance energy transfer", Journal of Analytical Science, vol. 34, Issue 6, Dec 20, 2018, pp. 815-818. (with English abstract provided entitled "Electrochemiluminescent Determination of Paracetamol Based on Resonance Energy Transfer Through Molecularly Imprinted Membrane").

* cited by examiner

REAL TIME WESTERN BLOT ASSAYS UTILIZING FLUORESCENCE RESONANCE ENERGY TRANSFER (FRET)

CROSS-REFERENCES TO RELATED APPLICATIONS

This application is a continuation of U.S. application Ser. No. 16/163,136, filed Oct. 17, 2018, now U.S. patent Ser. No. 11/604,186 issued Mar. 14, 2023, which is incorporated by reference herein in its entirety.

TECHNICAL FIELD

The present invention generally relates to Western Blot assays. In particular, the invention relates to Western Blot assays in which measurements of target proteins are performed in real time, and Western Blot assays based on fluorescence resonance energy transfer (FRET) events.

BACKGROUND

Western Blot is a type of analytical assay extensively utilized in areas of life sciences to identify, detect and measure target proteins in a sample and thereby obtain information regarding, size, integrity, modification, and identity. For example, a post-translational modification such as single or multiple phosphorylations of a single target protein or selected group of proteins, or all phosphorylated proteins can be confirmed, qualified and quantified. Biomarkers or differentially expressed proteins in known and unknown synthetical, biological or environmental samples (cell, tissue, body fluids, faeces, organ, whole organism, cell-free or enzyme based protein expression systems, sewage, soil, grain, food, etc.) can be identified.

In a typical, conventional Western Blot assay, a sample containing a mixture of target proteins (the proteins of analytical interest) and non-target proteins is subjected to gel electrophoresis to separate the proteins typically on the basis of their differing sizes or molecular weights. The separated proteins are then (typically electrophoretically) transferred to a membrane. A probing (or staining) procedure is then carried out on the membrane, which is often a two-step procedure. First, primary antibodies are added to the membrane, which bind specifically to the target proteins that were previously attached to the membrane by the transfer step. Second, secondary antibodies are added to the membrane, which bind specifically to the primary antibodies. The secondary antibodies are provided with chromophores or enzymes (typically fluorophores such as CY5® or other Cynanine dyes, Fluorescein, Rhodamine, or enzymes like alkaline phosphatase or horse radish peroxidase) linked to them. Thus, the probing procedure results in the target proteins being labeled and ready for interrogation by fluorescent, colorimetric or chemiluminescent detection. Before carrying out the probing procedure, a blocking agent is added to the membrane to prevent the primary antibodies from binding to the membrane instead of to the target proteins. Separate washing steps must be carried out after adding the blocking agent, the primary antibodies, and the secondary antibodies, respectively, to remove excess, unbound blocking agent and antibodies from the membrane.

The membrane containing the mixture of proteins, including the labeled target proteins, is then loaded into a detection instrument such as a fluorescence detection instrument. The instrument is then operated to irradiate the membrane (and thus the proteins) with light at a specific wavelength that induces fluorescence in the fluorophores associated with the target proteins. In response, the fluorophores emit light, the intensity of which is measured by the instrument. The detection signal produced in this manner may be utilized to derive various types of information regarding the target proteins detected, as appreciated by persons skilled in the art.

The Western Blot assay is time consuming as it requires several sequential steps (blocking, washing, incubation, etc.) to reach the final result, i.e. the endpoint measurement by which data are acquired. The Western Blot assay also requires a considerable variety and amount of consumable materials but most importantly repeated experiments of trials and errors to find optimal binding, washing, and detection conditions. The incubation times and buffer/solutions required depend on the effectiveness, binding affinity, selectivity, and sensitivity of the antibodies and antibody pairs utilized, the amount and quality of target protein involved (e.g., the expression level in different cells or tissues, proteolytic degradation, post-translational modifications, purity, stability, monomeric or multimeric state, etc.), the type of organism from which the sample is derived, the cell state (e.g., diseased or healthy, treated with a reagent or non-treated, etc.), pre-treatments by heat, chemicals, enzymes, additional purification, concentration by filtration/centrifugation/size exclusion, adsorption, enrichment or depletion of unwanted/unspecific proteins and the overall reagent setup. Nonetheless, Western Blot remains a very popular and widely utilized assay technique due to the useful data it produces. For many scientific areas, there is no practical technical alternative to Western Blot, and thus it is often considered the gold standard for scientific work and an essential requirement for scientific publications.

In addition to being time consuming, the conventional Western Blot assay may be characterized as being an "endpoint" measurement. This means that all data are obtained only after finishing the experiment, e.g., completing all of the steps described above and ending with the fluorescence detection. In particular, the probing procedure and the detection procedure are decoupled from each other and implemented separately. Hence, during the course of the assay, no data are obtained. Thus, the effects of intermediate steps of the assay, such as antibody binding, incubation, and washing, remain unknown, and no intervention can be made by the researcher in response to such effects. If the experimental design of the assay is incorrect or not optimized, the endpoint data will be negative (i.e., no detection at all of target proteins), or problematic (e.g., multiple proteins, such as both target and non-target proteins, are detected), or incorrect (e.g., detection is unspecific—the wrong proteins are detected) or unsatisfactory (specific band is too weak or borderline). The current general solution to this problem is to repeat the entire Western Blot assay as many times as needed, and/or to carry out several assays in parallel with different experimental parameters, to find the best conditions for the experiment and obtain useful data. Even then, however, only a few experimental parameters are changed and evaluated, and there still is no guarantee of successfully optimizing the assay. Moreover, the endpoint nature of the conventional Western Blot assay still remains, and hence information regarding the kinetics of the assay remain unknown and thus cannot be utilized to improve the assay or obtain the best data for a given sample and experimental conditions.

Therefore, it would be desirable to provide a method for Western Blot assaying that addresses the problems noted above.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to an embodiment, a method for performing a Western Blot assay includes: providing a sample supported on a membrane, the sample comprising a plurality of proteins, the plurality of proteins comprising a plurality of target proteins; performing a probing process by contacting the sample with a fluorescent resonance energy transfer (FRET) solution and allowing the probing process to proceed for a probing time period, wherein: the probing process produces a plurality of labeled target proteins to which first probes and second probes are bound; the first probes each comprise a donor chromophore, the second probes each comprise an acceptor chromophore, and the donor chromophore and the acceptor chromophore are effective as a donor-acceptor pair for FRET; and the FRET solution comprises the first probes, or the second probes, or both the first probes and the second probes; and while performing the probing process, measuring the labeled target proteins by: while performing the probing process, measuring the labeled target proteins by: irradiating the membrane with an excitation light to excite the donor chromophores, wherein in each labeled target protein, the excited donor chromophore transfers energy to the acceptor chromophore by FRET and, in response, the labeled target protein emits an emission light; and measuring an intensity of the emission light.

Other devices, apparatuses, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

As used herein, the term "sample" generally refers to a biological or environmental material known or suspected of containing one or more proteins of interest. The sample may be naturally occurring or synthetic. The sample may be used directly as obtained from the source or following a pretreatment to modify the character of the sample. The sample may be derived from any biological source, such as a cell, tissue, organ, whole organism, faeces, cell-free or enzyme-based protein expression systems, or physiological fluid such as blood, interstitial fluid, saliva, ocular lens fluid, cerebral spinal fluid, sweat, urine, milk, ascites fluid, raucous, synovial fluid, peritoneal fluid, vaginal fluid, amniotic fluid or the like. The sample may be pretreated prior to use, such as preparing plasma from blood, diluting viscous fluids, and the like. Methods of pretreatment can involve filtration, precipitation, dilution, distillation, concentration, inactivation of interfering components, chromatography, separation steps, and the addition of reagents. Besides physiological fluids, other liquid samples may be used such as water, sewage, soil, grain, food products and the like for the performance of environmental or food production assays. In addition, a solid material known or suspected of containing the protein(s) of interest may be used as the sample. In some instances it may be beneficial to modify a solid sample to form a liquid medium or to release the protein(s) of interest.

As used herein, the term "light" generally refers to electromagnetic radiation, quantizable as photons. As it pertains to the present disclosure, light may propagate at wavelengths ranging from ultraviolet (UV) to infrared (IR). In the present disclosure, the term "light" is not intended to be limited to electromagnetic radiation in the visible range. In the present disclosure, the terms "light," "photons," and "radiation" may be used interchangeably.

As used herein, a "chromophore" refers to a molecule (or moiety thereof) or atom that absorbs incident electromagnetic energy at a certain wavelength or wavelengths.

As used herein, a "fluorophore" refers to a chromophore that emits electromagnetic energy (emission light) at a certain wavelength in response to being irradiated by incident electromagnetic energy (excitation light) at a different wavelength. The wavelength of the emission light is typically longer than the wavelength of the excitation light, although may be shorter such as in the case of an upconverting phosphor (UCP).

Figure 1:
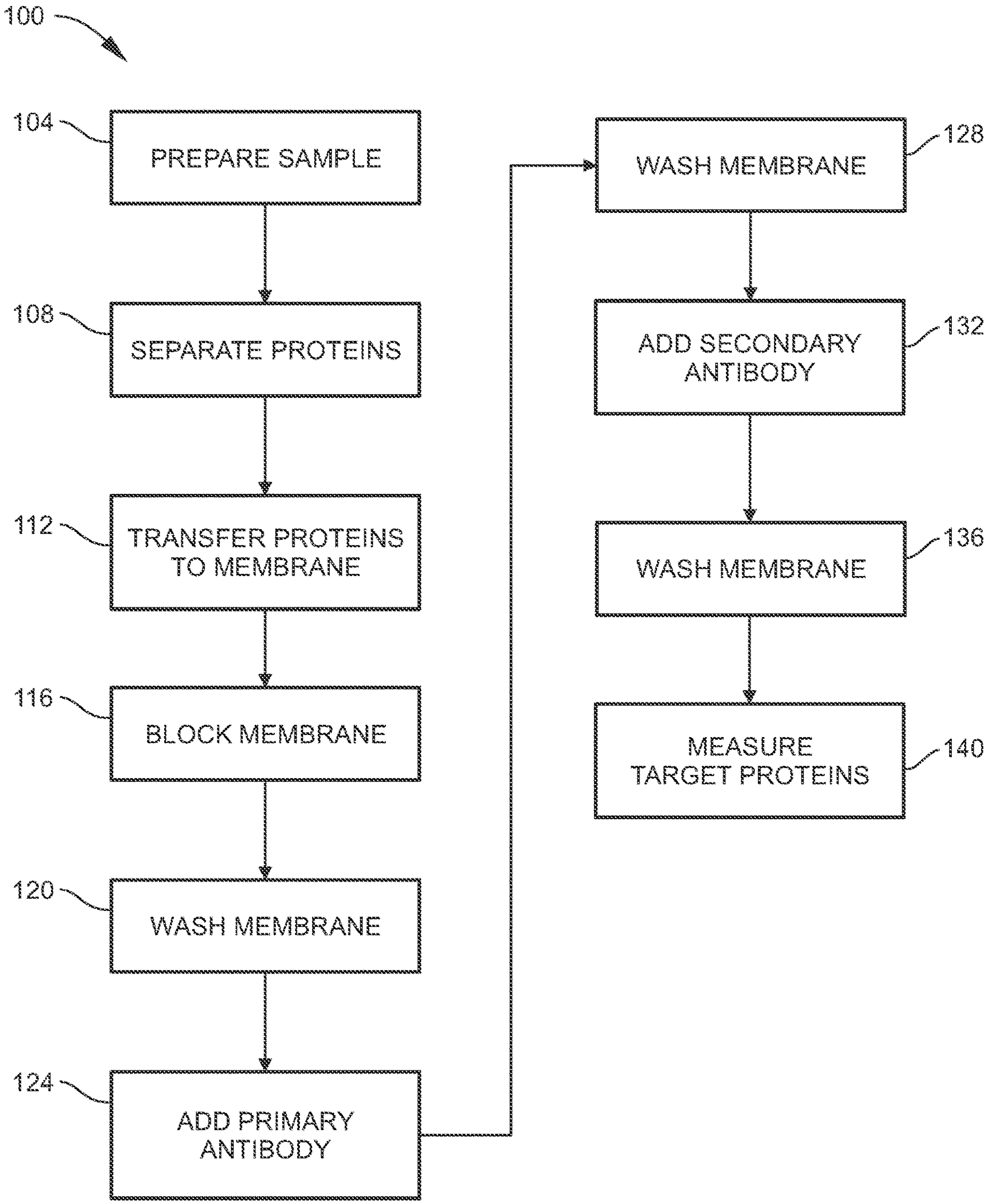
FIG. 1 is a flow diagram illustrating a conventional method for performing a Western Blot assay.

FIG. 1 is a flow diagram 100 illustrating a conventional method for performing a Western Blot assay. As an initial step, a sample containing a mixture of proteins is prepared as needed for electrophoretic separation (step 104). For example, the components of the sample may be acquired from tissue, a cell culture, a virus, an environmental sample, etc. The sample may be broken down or otherwise further processed as needed such as by utilizing a blender, homogenizer, sonicator, centrifuge, filter, etc. The resulting prepared sample is typically a mixture of proteins and cell lysate in solution. Buffers, reagents, or the like may be added to the solution as needed.

The sample is then loaded into an electrophoretic separation device and subjected to electrophoresis, whereby proteins having different attributes are spatially separated from each other (step 108). Depending on the electrophoretic separation technique utilized, the attribute on which the electrophoretic separation is based may be molecular weight (MW) or size, isoelectric point (pI), electric charge, or a combination of two or more of these attributes. Typically, the electrophoretic separation technique chosen is sodium dodecyl sulfate polyacrylamide gel electrophoresis (SDS-PAGE).

Figure 2:
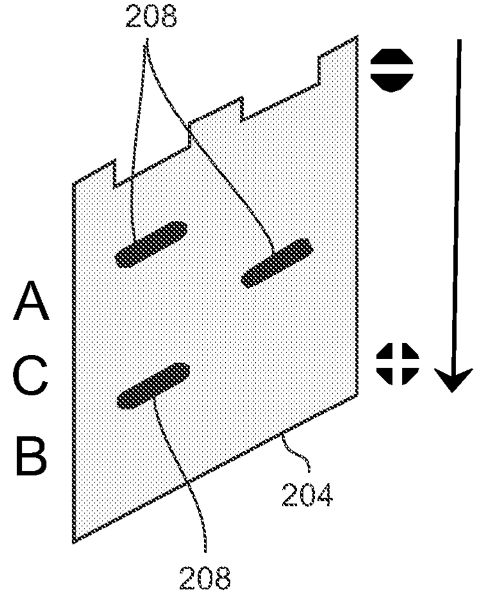
FIG. 2 illustrates an example of a protein separation process by SDS-PAGE that may be performed as part of a Western Blot assay.

FIG. 2 illustrates an example of a protein separation process by SDS-PAGE. A polyacrylamide gel is disposed on a support plate 204. The sample is loaded into one or more lanes of the gel and becomes covered by the negatively charged SDS. The support plate 204 is mounted between a negatively charged cathode and a positively charged anode. A voltage is applied between the cathode and the anode, as indicated by positive (+) and negative (−) signs in FIG. 2. Consequently, proteins migrate through the lanes of the gel toward the positively charged anode (as depicted by an arrow in FIG. 2) at different speeds dependent on their different electrophoretic mobilities (based on size or other attribute). For example, smaller proteins will migrate through the gel faster than larger proteins. This results in the different proteins spatially separating into bands 208 in each lane.

As an alternative to separation along one dimension (or direction), the gel electrophoresis technique may be configured to separate proteins along two dimensions (2-D gel electrophoresis), as appreciated by persons skilled in the art. For example, proteins may be separated according to molecular weight along one dimension and according to isoelectric point along another dimension.

Referring again to FIG. 1, after the gel electrophoresis is complete, the separated proteins are transferred to a membrane suitable for immunostaining (step 112). The membrane is made of a material exhibiting non-specific protein binding—that is, all proteins will bind to the membrane material equally well (without preference for any specific type of protein). Typical membranes are made of nitrocellulose or polyvinylidene difluoride (PVDF). The protein transfer technique is configured such that the spatially separated arrangement of the proteins is maintained after transfer is complete. Protein transfer, or blotting, is typically done by electroblotting.

Figure 3:
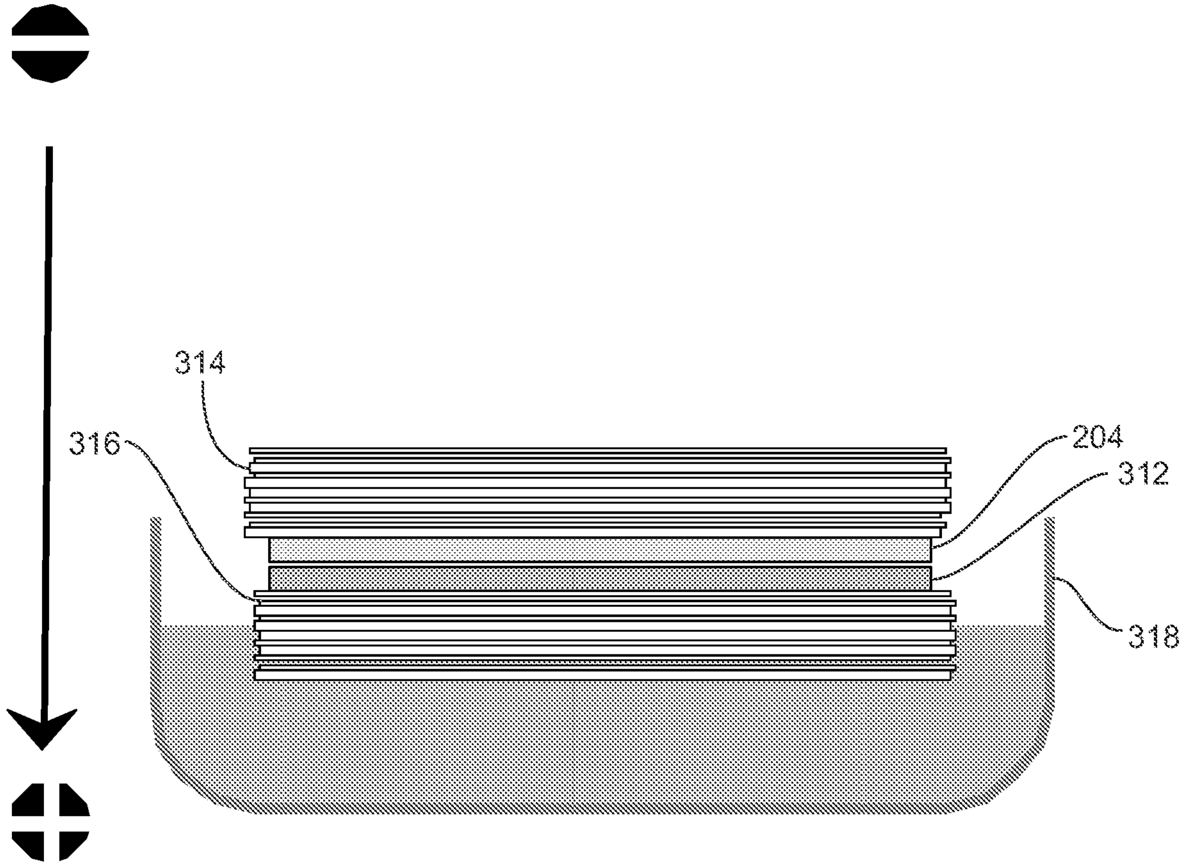
FIG. 3 illustrates an example of a protein transfer process that may be performed as part of a Western Blot assay.

FIG. 3 illustrates of an example a protein transfer process that may be performed as part of a Western Blot assay. The support plate 204 containing the gel and separated proteins is positioned adjacent to a membrane 312. The support plate 204 and the membrane 312 may stacked between filter papers 314 and 316, and the stack of components may be placed in a transfer buffer. Similar to the electrophoretic separation process, a voltage is applied between a negatively charged cathode and a positively charged anode, whereby the proteins are pulled from the gel onto the membrane 312.

Figure 4:
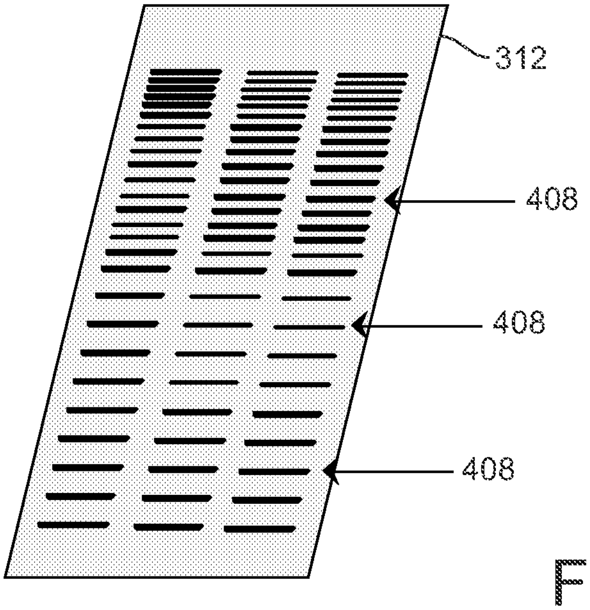
FIG. 4 illustrates of an example of a membrane after the protein transfer process illustrated in FIG. 3.

FIG. 4 illustrates an example the resulting membrane 312 after the protein transfer process is complete and the membrane 312 has been removed from the blotting apparatus. The membrane 312 contains transferred proteins 408 with their spatial separations preserved.

Referring again to FIG. 1, after the protein transfer process is complete, a blocking step is performed (step 116) in preparation for probing the membrane 312 for target proteins (the proteins of interest). Blocking entails adding a blocking agent to the membrane 312. The blocking agent has a composition effective for preventing the antibody probes intended for binding to the target proteins from instead binding to the membrane 312. Typically, the blocking agent is a solution of proteins such as non-fat dry milk or bovine serum albumin (BSA). These blocking proteins bind to the locations on the membrane 312 where the proteins are not bound (from the protein transfer process) or absent at all, or sticky proteins in samples are blocked, thereby preventing the subsequently added antibody probes from binding to the membrane 312. In this way, the blocking step reduces background noise and false positives during the subsequent process of measuring the target proteins.

After blocking, a washing step is performed to remove excess blocking agent and unbound proteins from the membrane 312 (step 120). A suitable wash buffer is utilized for this purpose.

After blocking and washing, a solution containing primary antibody is added and incubated with the membrane 312 (step 124) using a suitable incubator. Incubation is done for a period of time (e.g., a few hours or overnight) and at a controlled temperature (and possibly agitation) sufficient for specific binding to occur between the primary antibodies and the target proteins. The primary antibody is configured (e.g., in terms of its composition or structure) to bind only to the target protein by recognizing a specific epitope of the target protein. Ideally, minimal or no non-specific binding (binding between the primary antibodies and non-target proteins) occurs, as non-specific binding contributes only to background noise and not to the actual analytical detection signal to be acquired during the subsequent measurement process.

After incubating with the primary antibody, another washing step is performed to remove unbound primary antibody from the membrane 312 (step 128). A suitable wash buffer is utilized for this purpose.

After incubating with the primary antibody and washing, a solution containing secondary antibody is added and incubated with the membrane 312 (step 132). The process of incubation with the secondary antibody is similar to the process of incubation with the primary antibody. Incubation is done for a period of time (e.g., one or a few hours) and at a controlled temperature (and possibly agitation) sufficient for specific binding to occur between the secondary antibodies and the primary antibodies. The secondary antibody is configured to bind only to the primary antibody, with minimal or no non-specific binding occurring between the secondary antibody and other proteins on the membrane 312. The secondary antibody is labeled with an appropriate fluorescent label to enable detection of the target proteins by a fluorescence-based technique. To enable detection by time-resolved fluorescence (TRF), a fluorescent label with a long emission lifetime (e.g., microseconds to milliseconds) is selected, for example a lanthanide such as a europium (Eu(III)) or terbium (Tb(III)).

After incubating with the secondary antibody, yet another washing step is performed to remove unbound secondary antibody from the membrane 312 (step 136). A suitable wash buffer is again utilized for this purpose.

After incubating with the secondary antibody and washing, the target proteins are measured (step 140) by, for example, a fluorescence-based technique such as TRF. Measurement of the target proteins may be done by loading the membrane 312 into a fluorescence measurement instrument, which may be a dedicated fluorimeter or a multimode reader capable of fluorescence-based measurement.

Figure 5:
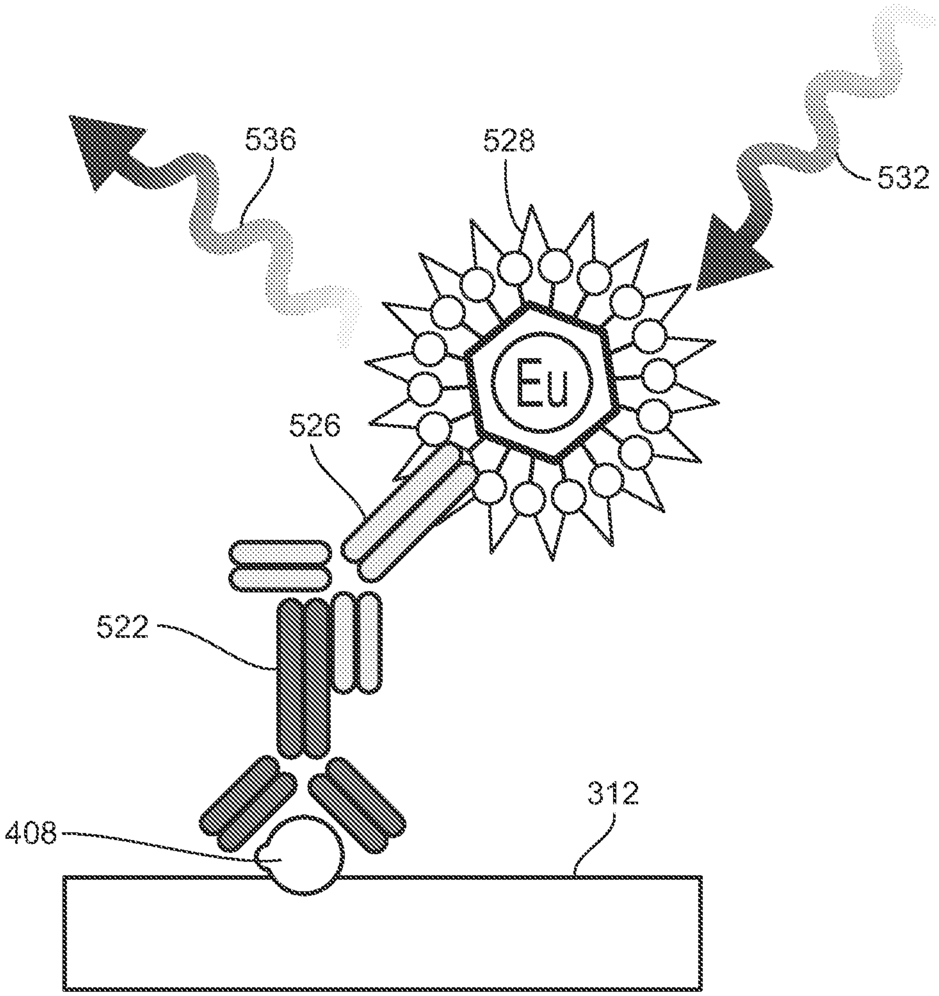
FIG. 5 is a schematic diagram illustrating a Western Blot assay utilizing fluorescence measurement.

FIG. 5 is a schematic diagram illustrating a Western Blot assay utilizing fluorescence measurement. FIG. 5 illustrates one of the target proteins 408 that is bound to the membrane 312. A primary antibody 526 is bound to the target protein 408, and a secondary antibody 528 labeled with a fluorescent label 528 is bound to the primary antibody 526. The measurement step 140 (FIG. 1) entails scanning the membrane 312 for target proteins 408 by irradiating the membrane 312 with an excitation light 532. The excitation light 532 propagates at a wavelength effective to induce fluorescence in the fluorescent labels 528, which are attached only to the target proteins 408 as shown in FIG. 5. In the response to irradiation by the excitation light 532, the fluorescent label 528 emits emission light 536 at a different (usually longer) wavelength than the excitation light 532. The emission light 536 constitutes the detection signal utilized by the measurement instrument to detect the target proteins 408. The emission light 536 is received by an appropriate light detector of the measurement instrument, such as a photomultiplier tube (PMT). The light detector measures the intensity of the emission light 536 received. The intensity measurement may be correlated with the amount or concentration of target proteins 408 in the sample, and/or utilized to derive other information regarding the target proteins 408.

As noted earlier in this disclosure, a conventional Western Blot such as the example described above is disadvantageous due to being an "endpoint" measurement. That is, measurement of the detection signal emitted from the target proteins is done only at an endpoint, which is a predetermined point in time that is often fixed (the same) for different assays (having different samples, probes/labels, and/or other experimental parameters). Thus, the endpoint (and accordingly the endpoint measurement) often is not optimized for any one particular assay. The endpoint is often assumed to occur after the incubation (probing) process has reached its chemical equilibrium, for example after the desired antibody binding has been completed. In actual practice, however, the incubation process is a dynamic process in which the reactants (probes and proteins) interact in forward and reverse directions (e.g., association and dissociation) as they try to reach an equilibrium or homeostasis. Moreover, the conventional Western Blot requires the endpoint measurement to be made only after all liquid has been removed from the sample (i.e., the washing steps). The liquid removal/washing effectively stops or freezes the incubation process (the probe-protein interactions), irrespective of whether equilibrium has been reached. Thus, the endpoint measurement often is taken at a time when the probe-protein interactions are incomplete, particularly if the assay involves weak interactions that are slow or prone to reversal or dissociation. Further, antibodies (or other types of molecules utilized to probe for target proteins) differ in affinity, selectivity, specificity, stability, purity, and quality. The variances in these attributes influence the performance of the antibodies in the Western Blot assay and the quality of the detection signal obtained from the assay. However, these essential parameters are not able to be considered in the conventional Western Blot, again because it is a merely an endpoint measurement that is taken after halting the incubation process.

Consequently, in the conventional Western Blot, a single specific band of target proteins is detected in the best case, or no band at all is detected in the worst case, or multiple bands are detected that are either all unspecific bands or a single specific band and multiple unspecific bands. The reason is that the antibody solutions are not applied under the best condition for all cases. For example, weak affinity of an antibody for the target protein will result in rapid dissociation of the antibody from the target protein, which may occur before the endpoint measurement is made. Both too short and too long incubation times may be problematic. If the incubation period is too short, an insufficient amount of specific binding between the antibodies and the target proteins may occur. If the incubation period is too long, unspecific antibodies may bind to more proteins, and/or unselective antibodies may bind to non-target proteins having epitopes similar to those of the target proteins, and/or excessive dissociation may occur between antibodies and target proteins. In all such cases, the endpoint measurement implemented by the conventional Western Blot may not provide the best or most comprehensive data for a given assay.

The present disclosure addresses these problems by providing a Western Blot assay that is kinetic or dynamic in nature rather than being an endpoint experiment. In this way, the detection signal may be evaluated (and the best data may be found) in real time, without needing to wait until the entire assay has been completed. The Western Blot assay of the present disclosure is a homogenous, "mix-and-measure" assay in which the probing and measurement procedures are coupled (i.e., not separated). The detection signal is acquired in real time while the probing procedure is being carried out. Moreover, the Western Blot assay disclosed herein eliminates several of the steps of the conventional assay, thus reducing the total amount of time required for the assay. In particular, separate steps for adding primary and second antibodies (or other types of probe molecules) are not required, and removal of unbound antibodies (or other types of probe molecules) is not required for the detection and measurement of the target proteins, thereby eliminating several washing steps. According to the present disclosure, the probing procedure may be carried out essentially in a single step, and essentially simultaneously with the measurement step if desired, thereby enabling the acquisition of a time-scan detection signal, i.e., a detection signal that varies over time in accordance with the kinetics of the probing process. In this way, the Western Blot assay disclosed herein enables the observation of the kinetic interactions involved in the probing process, including both association and dissociation, which depend on concentration, affinity, and time. Moreover, many bound and unbound states may be detected.

In addition, because the detection signal is acquired over time and the probe-protein interactions of the probing process are not halted by any washing/liquid removal steps, the measurement period of the present method may include the point in time at and near which the probing process has reached an interactional equilibrium, which may correspond to the maximum amount of target proteins being labeled. For many assays, the equilibrium point may be considered to be the optimal time for reading the sample to acquire the detection signal. Because the method disclosed herein generates a time-varying detection signal and enables the detection signal to be monitored in real time during the probing process, if desired, the measurement step or measurement period of the present method may be stopped (and/or the probing process may be stopped, such as by washing) at or near the equilibrium point. Moreover, the measurement period may include points or intervals of time prior to reaching equilibrium, thereby enabling the observation of various kinetics or activity of potential interest that may occur prior to reaching equilibrium. It will be noted that in the present context, the equilibrium may be a dynamic equilibrium at which the rates of association and dissociation between the probes and proteins become equal or approximately equal to each other, i.e. not necessarily zero.

Figure 6:
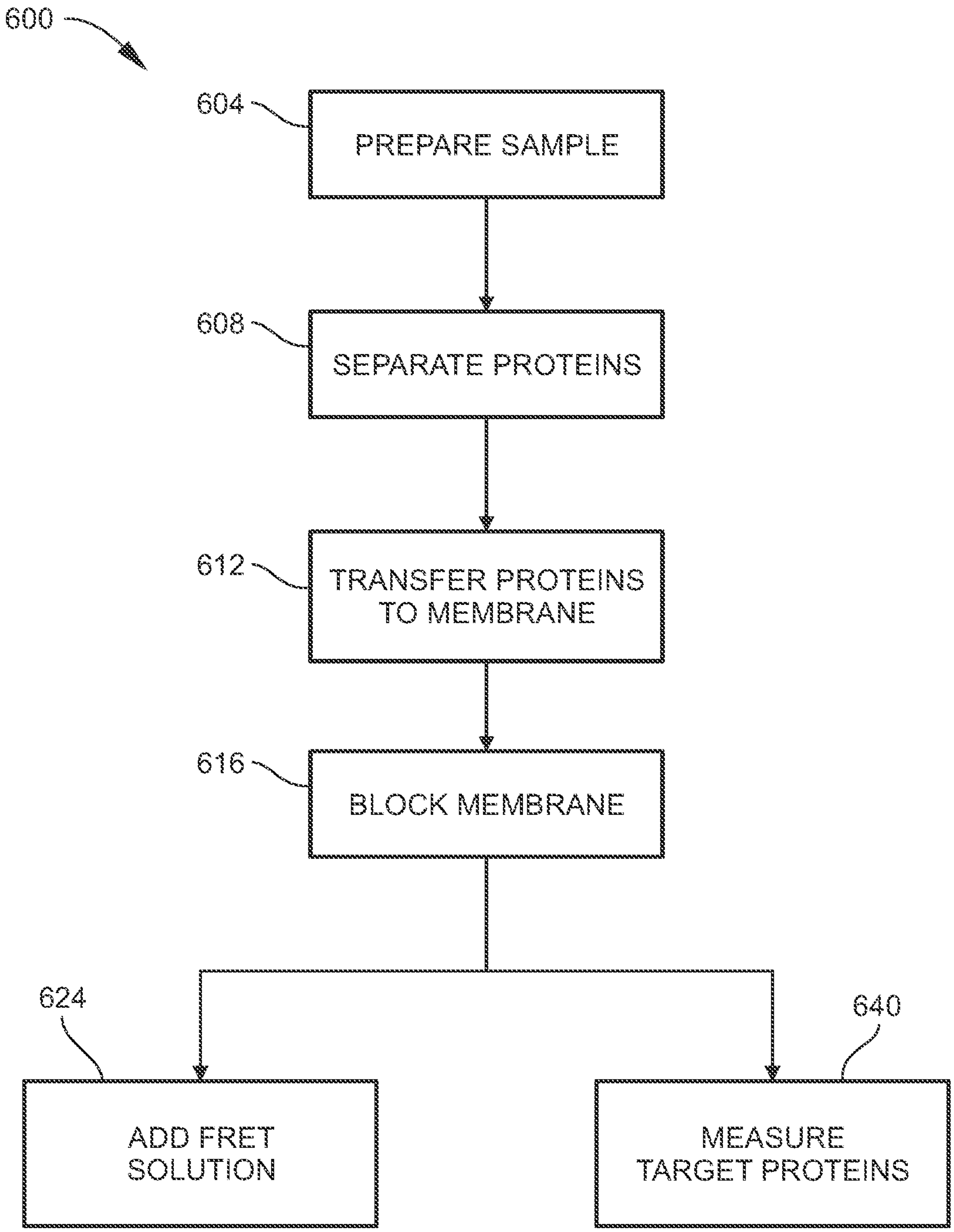
FIG. 6 is a flow diagram illustrating an example of a method for performing a Western Blot assay according to an embodiment of the present disclosure.

FIG. 6 is a flow diagram 600 illustrating an example of a method for performing a Western Blot assay according to an embodiment of the present disclosure. First, a sample containing a mixture of proteins supported on a membrane is provided. For this purpose, the initial steps of the method may be similar to those described above in conjunction with FIG. 1. Accordingly, a sample is initially prepared as needed for electrophoretic separation (step 604), the prepared sample is then loaded into an electrophoretic separation device and subjected to electrophoresis to separate different proteins from each other (step 608), the separated proteins are then transferred to a membrane suitable for immunostaining (step 612), and a blocking buffer solution is added (step 616) in preparation for probing the membrane for target proteins.

After blocking the membrane, a probing process is performed (step 624). According to the present disclosure, the probing process is initiated by contacting the sample with a fluorescent resonance energy transfer (FRET, also known as Förster resonance energy transfer) solution, after which the probing process is allowed to proceed for a probing time period. The probing process causes target proteins to be labeled with FRET donor-acceptor pairs, as described herein. While the probing process is being carried out, the labeled target proteins are measured (step 640), thereby producing a detection signal over time (as multiple detection points or intervals, or continuously). The duration of the probing time period may be initially predetermined as part of the method development for the specific assay being performed, and may be adjusted (in real time, if desired) based on the time-varying detection signal acquired as described herein.

In the present context, a FRET solution is a solution that includes a plurality of first probes (or donor probes) and/or a plurality of second probes (or acceptor probes) that are different (e.g., compositionally and/or structurally) from the first probes. Each first probe is or includes a first chromophore (or donor chromophore), and each second probe is or includes a second chromophore (or acceptor chromophore) that is typically different (e.g., compositionally and/or structurally) from the first chromophore. That is, the first probe may consist solely of the first chromophore, or may include at least one (other) molecule (which may be referred to herein as a "probe molecule") to which the first chromophore is attached (or bound, linked, conjugated, etc.) such as by a chemical bond or biological association or affinity. Likewise, the second probe may consist solely of the second chromophore, or may include at least one (other) molecule (which may be referred to herein as a "probe molecule") to which the second chromophore is attached (or bound, linked, etc.) such as by a chemical bond or biological association or affinity. The respective configurations (e.g., compositions, structures, etc.) of the first probe and the second probe are selected such that they will bind specifically to the target proteins of the sample. In particular, the first probe will bind to a first epitope of the target protein, and the second probe will bind to a second epitope of the same target protein. The first epitope and the second epitope are different, but are located at two different sites or loci on the same target protein. In this manner, the probing process results in the target proteins becoming labeled directly or indirectly (via a probe molecule such as an antibody) with the corresponding first chromophore and second chromophore.

In an embodiment, the FRET solution, at least when initially provided (i.e., before being added to the sample on the membrane), may include both the first (donor) probes and the second (acceptor) probes. In this case, the sample, at least when initially provided (i.e., before being contacted with the FRET solution) may include the proteins (both target proteins of interest and non-target proteins) without any probes present. In another embodiment, before contacting the sample, the FRET solution includes the first probes but not the second probes. In this case, the sample, before being contacted with the FRET solution, may have been prepared such that the second probes have already been added to the sample and bound to target proteins thereof. In another embodiment, before contacting the sample, the FRET solution includes the second probes but not the first probes. In this case, the sample, before being contacted with the FRET solution, may have been prepared such that the first probes have already been added to the sample and bound to target proteins thereof. In all such embodiments, the FRET solution has a composition (including first probes and/or second probes) such that, after contacting the sample, the probing process results in the target proteins becoming fully labeled with both the first chromophores and the second chromophores.

In a target protein so labeled, the corresponding first chromophore and second chromophore may be referred to as a donor/acceptor pair (or "FRET pair"). Generally, the donor and acceptor of a donor/acceptor pair are selected so as to be effective for FRET to occur between them, as described below. The first or donor chromophore is a fluorophore. The second or acceptor chromophore may also be a fluorophore, or may be a non-fluorescent chromophore, depending on the embodiment. The second chromophore if non-fluorescent may serve primarily as a quencher of fluorescent emission of the first chromophore (fluorophore), as described further below. Examples of chromophores suitable for use as FRET species are described below.

The FRET mechanism involves a distance-dependent transfer of energy from the donor (first chromophore) to the acceptor (second chromophore) via non-radiative dipole-dipole coupling, as appreciated by persons skilled in the art. Generally, there are four primary conditions or criteria for FRET to occur between a donor/acceptor pair. First, the donor and the acceptor must be in close proximity to each other. The required distance is typically 1-10 nanometers (nm) and more preferably 2-9 nm. The required distance may be quantified by considering the efficiency, E, of the FRET-based energy transfer, which is inversely proportional to the sixth power of the distance, r, between the donor and the acceptor, as follows:

$$E=R_o^6(R_o^6+r^6),$$

where $R_o$ is the Förster distance (or radius), which is the distance at which the energy transfer efficiency is 50% (i.e., half the energy is transferred). The magnitude of the Förster distance depends on the spectral/optical properties of the donor and the acceptor, including the spectral overlap integral noted below, as well as the refractive index, n, of the solution, as appreciated by persons skilled in the art. In the presently disclosed method, this distance criterion can be met as a result of the binding events that occur during the probing step 624 (FIG. 6), i.e., after adding the FRET solution and donor/acceptor pairs bind to the same target protein as described herein.

Second, the emission spectrum of the donor must overlap with the absorption (excitation) spectrum of the acceptor. The degree or extent to which these spectra overlap may be quantified by the spectral overlap integral, J, which depends on the spectral/optical properties of the donor and the acceptor, as appreciated by persons skilled in the art. Generally, the degree of spectral overlap of a donor/acceptor pair should be high enough for efficient energy transfer to occur, while at the same time the respective spectra of the donor and the acceptor should be different enough to be readily distinguishable by the measuring instrument utilized to read the FRET events.

Third, the donor and acceptor transition dipole orientations (the orientations of the donor emission dipole moment and the acceptor absorption dipole moment relative to each other) must be approximately parallel. In this manner, the resonance condition needed for energy transfer by FRET can be fulfilled.

Fourth, the fluorescence lifetime of the donor must be long enough to enable FRET to occur.

The respective configurations (e.g., compositions, structures, etc.) of the donor (first chromophore) and the acceptor (second chromophore) are selected such that they are effective as donor-acceptor pairs for FRET (i.e., they are compatible for FRET to occur between them). The selection may be made with the above-described conditions in mind, particularly the spectral overlap, including considerations of the excitation and emission wavelength maxima of the donor and the acceptor. Examples of chromophores that may be utilized as donors and/or acceptors for FRET include, but are not limited to, fluorescent proteins, fluorescent dyes, lanthanide (Ln(III)) metals (as may be provided as metal ion complexes, e.g., chelates or cryptates), transition metals (as may be provided as metal ion complexes, e.g., chelates or cryptates), upconversion phosphors (UCPs), quantum dots, and non-fluorescent quenchers. Various combinations of species from the foregoing classes of chromophores may be suitable as donor-acceptor pairs for FRET, as appreciated by persons skilled in the art.

Examples of fluorescent proteins include, but are not limited to, green fluorescent protein (GFP) and variants (derivatives) thereof such as cyan fluorescent protein (CFP), yellow fluorescent protein (YFP), and blue fluorescent protein (BFP); enhanced versions of the foregoing such as enhanced green fluorescent protein (EGFP), enhanced cyan fluorescent protein (ECFP), enhanced blue fluorescent protein (EBFP), and enhanced yellow fluorescent protein (EYFP); red fluorescent protein (RFP or dsRed) and modified versions of the foregoing such as monomeric red fluorescent protein (mRFP); and phycobiliproteins, such as phycoerythrin (PE) and allophycocyanin (APC). In the context of the present disclosure, a fluorescent protein may be attached to another protein to form a fusion protein.

Examples of fluorescent dyes include, but are not limited to, cyanine (e.g., CY3®, CY5®, etc.), fluorescein and derivatives thereof such as fluorescein isothiocyanate (FITC), fluorescein amidite (FAM), rhodamine and derivatives thereof such as tetramethylrhodamine (TRITC, i.e., a base rhodamine molecule functionalized with an isothiocyanate group (—N═C═S) replacing a hydrogen atom); 5-((2-aminoethyl)amino)naphthalene-1-sulfonic acid (EDANS); and fluorescent compounds containing a 5-(Dimethylamino)-1-naphthalenesulfonyl (Dansyl) group (also referred to herein as Dansyl compounds). Further examples include fluorescent dyes having excitation wavelength maxima at (or at about) 405 nm, 430 nm, 488 nm, 514 nm, 555 nm, 546 nm, 610 nm, 647 nm, 680 nm, 700 nm, and 750 nm. Examples of the latter include fluorescent dyes synthesized by chemical modification (including, e.g., sulfonation) of earlier known fluorescent dyes (e.g., cyanine, fluorescein, rhodamine, etc.) to improve their properties. Examples of such synthetic fluorescent dyes include members of the family of ALEXA FLUOR® dyes available from Thermo Fisher Scientific Inc., Waltham, Massachusetts, USA, such as ALEXA FLUOR® 405, ALEXA FLUOR® 430, ALEXA FLUOR® 488, ALEXA FLUOR® 514, ALEXA FLUOR® 546, ALEXA FLUOR® 555, ALEXA FLUOR® 610, ALEXA FLUOR® 647, ALEXA FLUOR® 680, ALEXA FLUOR® 700, and ALEXA FLUOR® 750; and members of the family of IFLUOR® (iFluor™) dyes having excitation wavelength maxima similar to the foregoing examples of excitation wavelength maxima (e.g., IFLUOR® 700), available from AAT Bioquest, Inc., Sunnyvale, California, USA; and ULIGHT® (ULight™) dye having an emission wavelength at 665 nm, available from PerkinElmer Inc., Waltham, Massachusetts, USA.

Examples of lanthanide metals include, but are not limited to, samarium (Sm(III)), dysprosium (Dy(III)), europium (Eu(III)), and terbium (Tb(III)).

Examples of transition metals include, but are not limited to, ruthenium (Ru(II)), osmium (Os(II)), and rhenium (Re (I)).

Lanthanides and transition metals are particularly useful as donors for performing time-resolved FRET (TR-FRET), as their emission lifetimes are much longer than the lifetimes of background fluorescence or scattered light. This enables the emission signal from the acceptor resulting from FRET to be measured after the interfering background signal has completely decayed, thereby improving the signal/noise (S/N) ratio. For convenience in the present disclosure, the term FRET encompasses the term TR-FRET, unless specified otherwise or the context dictates otherwise.

Examples of UCPs include, but are not limited to, lanthanide-doped or transition metal-doped inorganic compounds exhibiting anti-Stokes shift (i.e, upconversion). The inorganic compound may be a crystalline material that includes a transparent host lattice doped with one or more dopants that enable or enhance the upconversion activity. Examples of inorganic compounds forming the basis for certain UCPs include, but are not limited to, various halides (e.g., $NaYF_4$, $YF_3$, $LaF_3$), oxides (e.g., $Y_2O_3$, $ZrO_2$), and oxysulfides (e.g., $Y_2O_2S$, $La_2O_2S$). Examples of suitable dopants include, but are not limited to, trivalent lanthanide ions and transition metals such as erbium ($Er^{3+}$), thulium ($Tm^{3+}$), holmium ($Ho^{3+}$), praseodymium ($Pr^{3+}$), neodymium ($Nd^{3+}$) dysprosium ($Dy^{3+}$), ytterbium ($Yb^{3+}$), and/or samarium ($Sm^{3+}$). As another example, UCPs may be utilized as described by Riuttamaki, Terhi, *UPCONVERTING PHOSPHOR TECHNOLOGY: Exceptional Photoluminescent Properties Light Up Homogeneous Bioanalytical Assays*, University of Turku Publications (2011), the entire content of which is incorporated by reference herein. As another example, suitable UCPs may be SUNSTONE® UCP Nanocrystals manufactured by Intelligent Material Solutions Inc., Princeton, New Jersey, USA, and commercially available from Sigma-Aldrich, Inc., St. Louis, Missouri, USA.

Quantum dots generally encompass fluorescent, inorganic semiconductor nanoparticles (particles typically having a diameter of 2-10 nm, but may be larger) that can be attached to probe molecules in accordance with embodiments described herein. For the purposes and convenience of the present disclosure, the term "chromophore" or "fluorophore" encompasses quantum dots, unless specified otherwise or the context dictates otherwise. Quantum dots may be utilized as donors or acceptors. Generally, any type of quantum dot may be utilized in the method disclosed herein. The quantum dot may have a core-shell configuration, in which the core and the surrounding shell may have distinct compositions. The quantum dot may also include ligands attached to its outer surface, or may be functionalized with other chemical moieties for a specific purpose. Typically, the quantum dot selected is one that is water soluble or water solubilizable through an appropriate process, and is capable of being conjugated to a protein or a probe. For example, the quantum dot may have an outer (e.g., polymer) coating effective to provide or enhance water solubility and affinity for certain conjugates. The composition selected for the quantum dot may be based on a desired property such as band gap energy or wavelength sensitivity. Moreover, the size of the quantum dot may be selected to absorb a desired range of electromagnetic radiation. Generally for a given species of quantum dot below a critical size, a smaller size is more sensitive to shorter (bluer) wavelengths and a larger size is more sensitive to longer (redder) wavelengths.

Generally, with the foregoing considerations in mind, the quantum dot may be selected from various Group II-VI, Group III-V, Group IV, Group IV-VI, and Group V-VI materials. Examples include, but are not limited to, Group II-VI materials such as ZnS, ZnSe, ZnTe, ZnO, CdS, CdSe, CdTe, CdO, HgS, HgSe, HgTe, HgO, MgS, MgSe, MgTe, MgO, CaS, CaSe, CaTe, CaO, SrS, SrSe, SrTe, SrO, BaS, BaSe, BaTe, and BaO; Group materials such as $CuInS_2$, $Cu(In,Ga)S_2$, $CuInSe_2$, and $Cu(In,Ga)Se_2$; Group III-V materials such as AN, AlP, AlAs, AlSb, GaN, GaP, GaAs, GaSb, InN, InP, InAs, and InSb; Group IV materials such as Si, Ge, and C; Group IV-VI materials such as GeSe, PbS, PbSe, PbTe, PbO, SnSe, SnTe, and SnS; and Group V-VI materials such as $Sb_2Te_3$, $Bi_2Te_3$, and $Bi_2Se_3$. Transition metal compounds such as the oxides, sulfides, and phosphides of Fe, Ni, and Cu may be applicable. Examples of quantum dots further encompass binary, ternary, quaternary, etc. alloys or compounds that include the foregoing species (e.g., SiGe, InGaAs, InGaN, InGaAsP, AlInGaP, etc.). Other quantum dots may include other types of semiconducting materials (e.g., certain organic and polymeric materials). For a quantum dot having a core-shell structure, the shell may be composed of one of the foregoing species or other species, and the respective compositions of the core and the shell may be different as noted above.

A few further examples include quantum dots having peak emission wavelengths of 520 nm, 540 nm, and 560 nm. Additional examples include Qdot® nanocrystals available from Thermo Fisher Scientific Inc., Waltham, Massachusetts, USA. In one specific example, the quantum dot may have a core of cadmium selenide (CdSe) or cadmium telluride (CdTe) or the like, a shell of zinc sulfide (ZnS) or the like, and an outer coating of an amphiphilic polymer configured to promote water solubility and affinity for desired conjugates. See, e.g., Dennis and Bao, *Quantum Dot—Fluorescent Protein Pairs as Novel Fluorescence Resonance Energy Transfer Probes*, Nano. Lett., Vol 8, No. 5, American Chemical Society (2008), the entire content of which is incorporated by reference herein.

Examples of non-fluorescent quenchers include, but are not limited to, 4-(4-Dimethylaminophenylazo)benzoyl (also referred to as Dabcyl); 4-(4-diethylaminophenylazo)benzenesulfonyl (also referred to as Dabsyl); and 2,4-dinitrophenyl (also referred to as Dnp).

As noted above, various combinations of the foregoing species of chromophores may be suitable as donor-acceptor pairs for FRET. The selection of particular pairs of donors and acceptors for attachment to the same target protein will depend on the particular experiment being conducted. The instrumentation (e.g., light source(s), light detector(s), excitation filter(s), emission filter(s), etc.) will also be selected and/or configured accordingly, as appreciated by persons skilled in the art.

Figure 7:
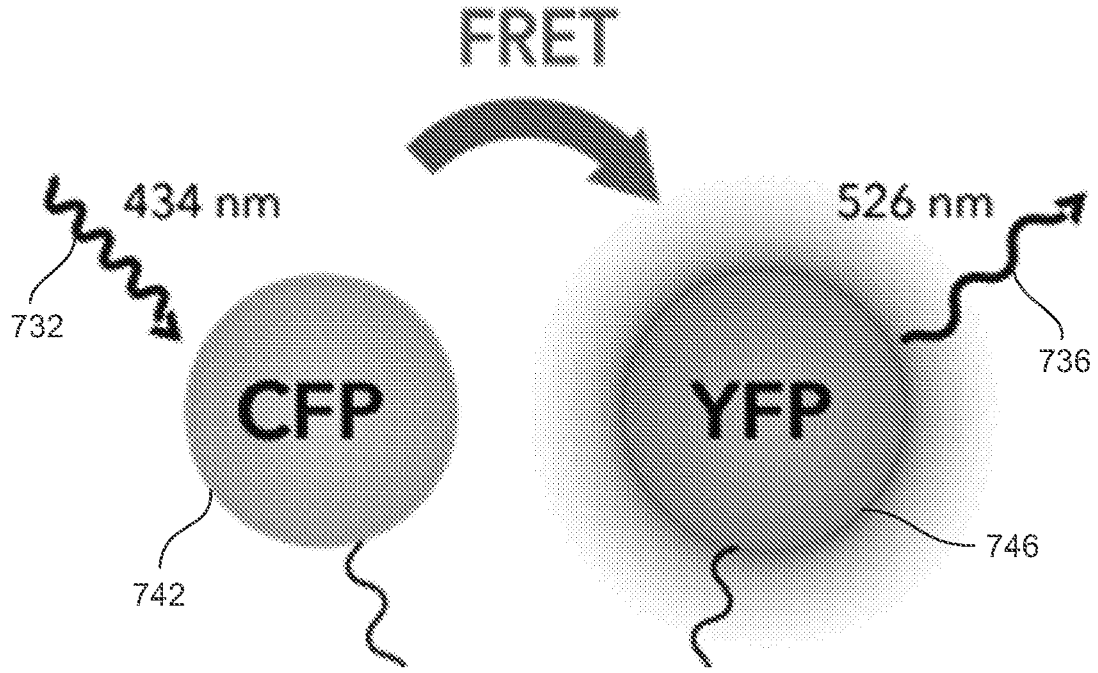
FIG. 7 is a schematic diagram illustrating an example of the FRET mechanism.

FIG. 7 is a schematic diagram illustrating an example of the FRET mechanism. A first (donor) chromophore 742 and a second (acceptor) chromophore 746 are positioned in close proximity to each other. The first chromophore 742 is irradiated with an excitation light 732 at an appropriate first wavelength to electronically excite the first chromophore 742. If the distance between the first chromophore 742 and the second chromophore 746 is close enough and the other conditions for FRET to occur described above are met, the first chromophore 742 transfers non-radiative energy to the second chromophore 746. In response, the second chromophore 746 if fluorescent emits emission light 736 at a second wavelength different from the first wavelength of the excitation light 732. The intensity of the emission light 736 can be measured by a suitable light detector as in the case of fluorescence detection techniques. As described above, the distance criterion for FRET to occur can be met by a first chromophore 742/second chromophore 746 pair binding to the same target protein during the probing process.

It will be noted that the non-radiative FRET-based energy transfer is different and separate from any fluorescent emission by the first chromophore 742 that may also occur in response to irradiation by the excitation light 732, and from the emission light 736 emitted by the second chromophore 746 in response to the FRET event, as appreciated by persons skilled in the art. That is, the FRET-based energy transfer itself is not fluorescence. However, the intensity of the emission light 736 from the second chromophore 746 may be utilized to detect the FRET event and may be correlated with the efficiency of the FRET.

Alternatively, the intensity of the emission light emitted by the first (donor) chromophore 742 in response to the irradiation of the first chromophore 742 with the excitation light 732 may be measured by the light detector. In this case, the quenching of the fluorescence of the first chromophore 742 (i.e., the decrease in intensity of fluorescent emission by the first chromophore 742) in response to FRET may be measured. Here, the second chromophore 746 may be one that serves merely as a quencher and may not itself be fluorescent (or its fluorescence may be filtered out or otherwise not measured), as described above. Similarly, a reduction in the excited state lifetime of the first chromophore 742 due to FRET may be measured.

Alternatively or in addition to the foregoing detection modes, both the emission light emitted by the first chromophore 742 and the emission light 736 emitted by the second chromophore 746 may be measured. Such measurement may be made using two different light detectors (sensitive to the two different emission wavelengths) if needed. As one example, a ratiometric measurement may be obtained from the two signals, which may provide useful information as appreciated by persons skilled in the art.

The foregoing detection modes may also be utilized to determine enzymatic cleavage events, such as in protease assays as appreciated by persons skilled in the art. For example, cleavage may result in the spatial proximity between the first chromophore 742 and the second chromophore 746 required for FRET no longer being met, i.e., the separation distance between the first chromophore 742 and the second chromophore 746 increases. Such event may be detected by, for example, measuring the resulting increase in fluorescence of the first chromophore 742 (due to quenching no longer occurring).

As described above, the probing process produces labeled target proteins to which the first probes and the second probes are bound. FIGS. 8A to 8D illustrate non-exclusive examples of different configurations of labeled target proteins that may be formed as part of a Western Blot assay, according to various embodiments of the present disclosure. In each embodiment, a first (donor) probe 852 and a second (acceptor) probe 856 are bound to a target protein 808. The first probe 852 is or includes a first (donor) chromophore 842, and the second probe 856 is or includes a second (acceptor) chromophore 846. The first probe 852 and/or the second probe 856 may also include probe molecules, such as antibodies, depending on the embodiment.

Figure 8A:
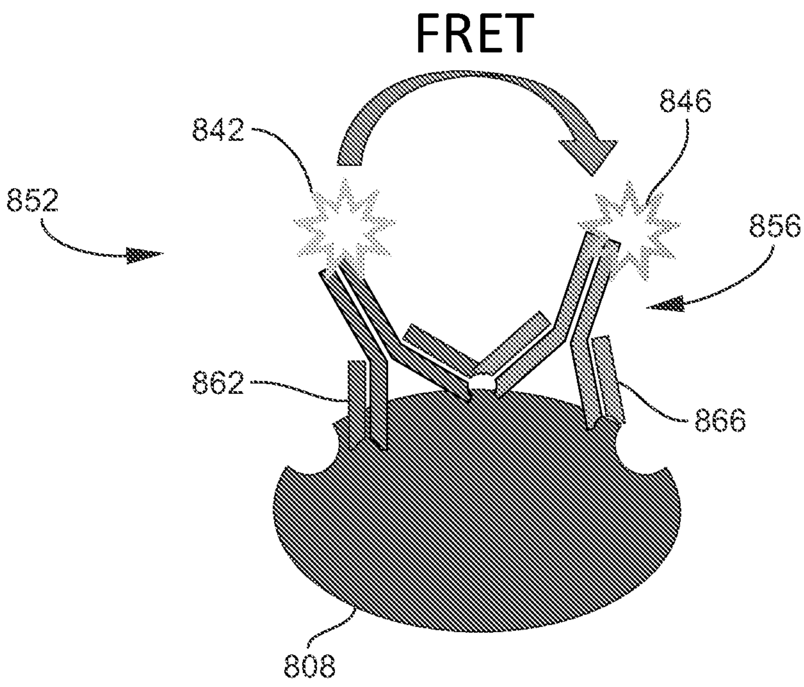
FIGS. 8A to 8D illustrate non-exclusive examples of different configurations of labeled target proteins that may be formed as part of a Western Blot assay, according to various embodiments of the present disclosure.

In the embodiment shown in FIG. 8A, the first probe 852 includes a first (donor) antibody 862 configured to bind directly to the target protein 808, and the first chromophore 842 is attached to the first antibody 862. The second probe 856 includes a second (acceptor) antibody 866 configured to bind directly to the target protein 808, and the second chromophore 846 is attached to the second antibody 866. As the first antibody 862 and the second antibody 866 are attached directly to (respective epitopes of) the target protein 808, they may be referred to as primary antibodies.

Figure 8B:
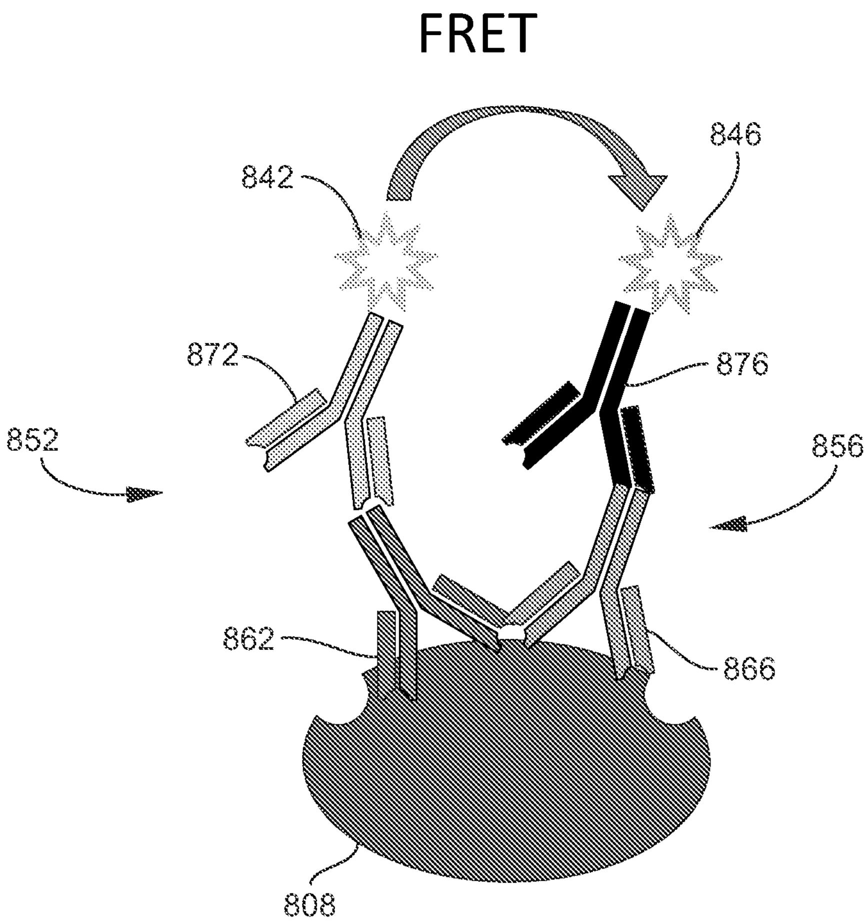

In the embodiment shown in FIG. 8B, the first probe 852 includes a first (donor) primary antibody 862 configured to bind directly to the target protein 808, and a first (donor) secondary antibody 872 configured to bind specifically to the first primary antibody 862. The first chromophore 842 is attached to the first secondary antibody 872. The second probe 856 includes a second (acceptor) primary antibody 866 configured to bind directly to the target protein 808, and a second (acceptor) secondary antibody 876 configured to bind specifically to the second primary antibody 866. The second chromophore 846 is attached to the second secondary antibody 876.

Figure 8C:
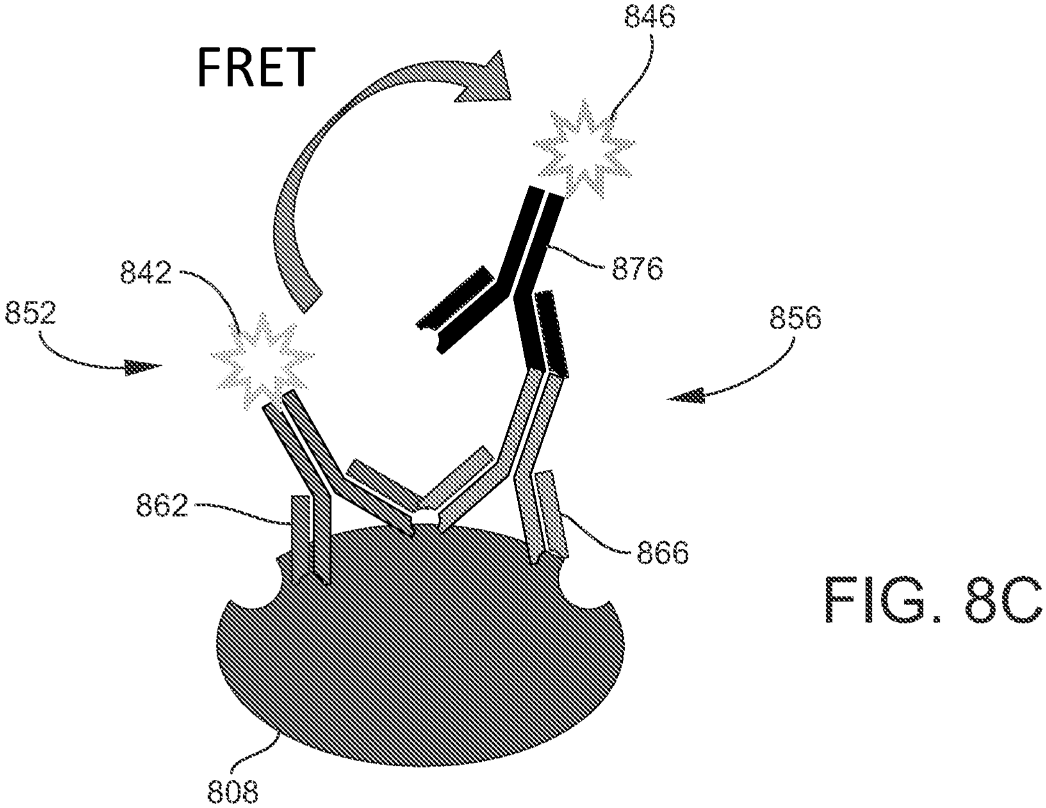

In the embodiment shown in FIG. 8C, the first probe 852 includes a first (donor) primary antibody 862 configured to bind directly to the target protein 808, and the first chromophore 842 is attached to the first primary antibody 862 (without a first secondary antibody). The second probe 856 includes a second (acceptor) primary antibody 866 configured to bind directly to the target protein 808, and a second (acceptor) secondary antibody 876 configured to bind specifically to the second primary antibody 866. The second chromophore 846 is attached to the second secondary antibody 876.

In an embodiment similar to that shown in FIG. 8C, the first probe 852 includes a first secondary antibody configured to bind specifically to the first primary antibody 862, and the first chromophore 842 is attached to the first secondary antibodies instead of directly to the first primary antibody 862. Also in this embodiment, the second chromophore 846 of the second probe 856 is attached directly to the second primary antibody 866 (without a second secondary antibody).

Figure 8D:
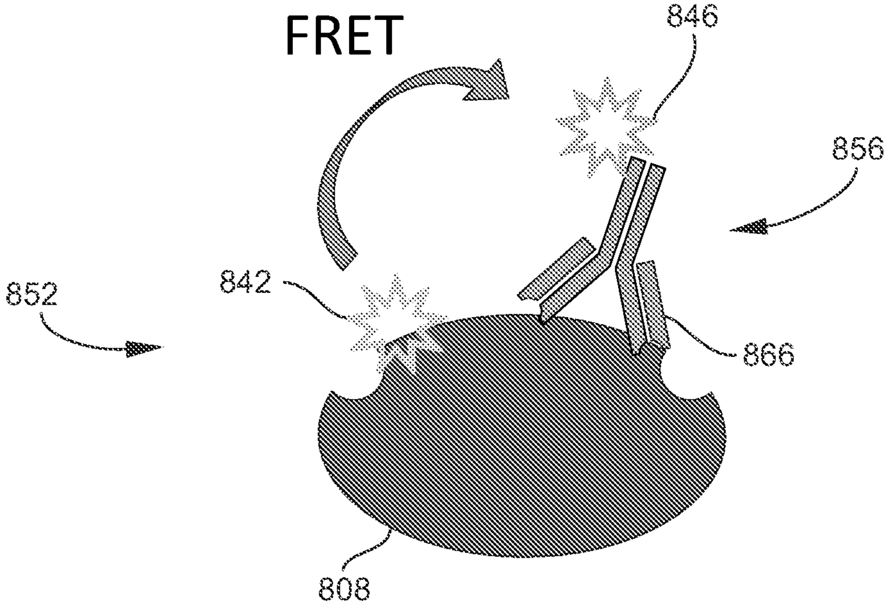

In the embodiment shown in FIG. 8D, the first probe 852 does not include any antibodies or other type of probe molecule. Instead, the first chromophore 842 is configured to bind directly to the target protein 808. The second probe 856 includes a second (acceptor) primary antibody 866 configured to bind directly to the target protein 808, and the second chromophore 846 is attached to the second primary antibody 866.

In an embodiment similar to that shown in FIG. 8D, the first probe 852 includes a first (donor) primary antibody 862 configured to bind directly to the target protein 808, and the first chromophore 842 is attached to the first primary antibody 862. The second probe 856, however, does not include any antibodies or other type of probe molecule. Instead, the second chromophore 846 is configured to bind directly to the target protein 808.

Thus, in embodiments such as represented by FIG. 8D, a chromophore (e.g., first chromophore 842) may already be attached to the target protein 808 at the time the sample is provided, i.e., prior to adding the FRET solution to the sample to fully label the target protein 808 with a donor/acceptor pair as part of the method disclosed herein. Such chromophore may already be directly attached to the target protein as part of preparing the sample, or even before preparing the sample, for the Western Blot assay disclosed herein. As examples, the chromophore may be a fluorescent substrate of an enzyme, or may be a fluorescent ligand of a transporter protein, or may be part of the target protein (e.g., genetically engineered fluorescent protein fusions), or may be pretreated with the target protein (e.g., chemically conjugated proteins), or may be a metabolically produced fluorescent intermediate binding to a target protein (e.g. fluorescent prodrugs bound to receptor proteins, such as a target protein within a cell after getting metabolized by other proteins). Generally, a chromophore-bound target protein may be obtained from treated cells (in-cell labelling) or in vitro from cell-free proteins by biological or chemical labelling methods, or in vivo by treating organisms (e.g. animals) before obtaining samples for Western Blot analyses.

As used herein, the term "antibody" (Ag), or immunoglobulin (Ig), refers to a Y-shaped protein according to its usual meaning as generally understood by persons skilled in the art. Generally, any antibodies, antibody fragments and domains (ScFv, Fab, dAb, diabodies, nanobodies, and artificial variants thereof, as well as non-immunoglobuline proteins) capable of functioning as probes in the method disclosed herein may be utilized. As one non-exclusive example, in the configuration shown in FIG. 8B, the first primary antibody 862 may be a mouse antibody, the first secondary antibody 872 may be a goat anti-mouse antibody, the second primary antibody 866 may be a rabbit antibody, and the second secondary antibody 876 may be a donkey anti-rabbit antibody.

More generally, in addition to or as an alternative to antibodies, the first probe 852 and/or second probe 856 may be or include other types of probe molecules capable of functioning as probes in the method disclosed herein. Examples of other types of probe molecules may include, but are not limited to, streptavidin, avidin, non-immunoglobulin (non-Ig) proteins (or domains or fragments of proteins), (poly)peptides, nucleic acids (e.g., deoxyribonucleic acid or DNA, ribonucleic acid or RNA), sugars or other types of carbohydrates, fatty acids or other types of lipids, and small molecules of appropriate configuration. One non-exclusive example of a small molecule is biotin, which binds with high affinity and specificity to streptavidin or avidin, as in the capturing of biotinylated proteins as appreciated by persons skilled in the art. Other non-exclusive examples of small molecules include those that can be labeled with boron-dipyrromethene (BODIPY) fluorescent dyes, such as 1,25-dihydroxycholecalciferol (calcitriol) and steroids such as estrogen, androgen, etc.

Referring again to FIG. 6, the probing process (step 624) is initiated (and thus the probing time period starts) by adding the FRET solution to the sample, i.e. contacting the sample with the FRET solution. During the probing process (hence during the probing time period), the unbound probes provided with the FRET solution become associated with the target proteins via specific binding events. For this purpose, the probing process may be carried out under controlled incubation conditions (e.g., temperature, pressure, etc.) and utilizing appropriate hardware (or labware) as needed, and as appreciated by persons skilled in the art. The probing time period, i.e. the duration of the probing process (step 624), may be as long as needed for the target proteins 808 of the sample to be labeled with the donor-acceptor pairs, and for a time-varying detection signal to be acquired. As one non-exclusive example, the duration of the probing time period (starting with adding the FRET solution) may be in a range from 5 minutes (min), 10 min, 20 min, 30 min, 60 min (1 hour (hr)), 2 hrs, 4 hrs, 6 hrs, 8 hrs, 10 hrs, 12 hrs, 14 hrs, 16 hrs, 18 hrs, 20 hrs, 22 hrs, and 24 hrs.

According to the method, the labeled target proteins 808 are measured (step 640) while performing the probing process (step 624). In other words, the target proteins 808 are measured during all or part of the probing time period. In still other words, the target proteins 808 are measured during a measurement time period that overlaps at least partially with the probing time period. Initiation of the measurement time period may occur at the same time as, or at some time after, initiation of the probing time period. That is, the measurement of the emission signal(s) may be initiated simultaneously or substantially simultaneously with contacting the sample with the FRET solution. The measurement time period may end (measurement may be stopped) before, at the same time as, or after the probing time period ends (is stopped). Thus, in the method disclosed herein, measurement is coupled with the probing process. This is in contrast to the conventional, single endpoint measurement, which is taken after completion of the probing process as noted above.

In some embodiments, measuring the intensity is initiated after a delay period following contacting the sample with the FRET solution. The delay period may be implemented, for example, to enable time-resolved measurement as described herein. In such case, the delay period may be long enough to allow background fluorescence and other short-lived sources of noise to decay significantly. As a non-exclusive example, the delay period may have a duration of 1 second or less, such as on the order of microseconds.

Measuring the target proteins 808 entails irradiating the membrane (and thus the sample supported by the membrane, including the separated proteins of the sample) with an excitation light 732 (FIG. 7) to excite the first chromophores 842. In the irradiated target proteins that have been successfully labeled also with the second chromophores 846, the excitation induces FRET, i.e., the excited first chromophore 842 transfers energy to the second chromophore 846 of the same donor-acceptor pair by FRET. In response, the second chromophore (if a fluorophore) emits an emission light 736 (FIG. 7). The intensity of the emission light 736 is measured. The measurement may be correlated with the concentration of target proteins detected in the sample, and utilized to derive other information regarding the target proteins as appreciated by persons skilled in the art. Alternatively or additionally, emission light from the first chromophore 842 may be measured, as described above.

As described above, by coupling the probing process and the measuring process, the method produces a time-scan detector signal in which the intensity of the detector signal varies over time in accordance with the varying conditions of the probing process. Acquiring the detector signal dynamically, or in real time, provides useful information regarding the kinetics of the probing process (and the entire probing process if desired), and allows the binding activity (both association and dissociation) to be monitored on a continuous (real time) basis, as well as ensuring the acquisition of data at and/or near equilibrium. Further, the dynamic data acquisition facilitates optimizing a given assay for a given set of conditions, such as for a particular target protein, sample, instrument, operating parameters, etc. Notably, performing the probing process and measuring the intensity of the emission light is done without needing to first remove unbound first probes, unbound second probes, or other materials and liquid from the sample. This is in contrast to the non-homogeneous setting of the conventional Western Blot, which would not allow dynamic data acquisition to be possible.

Figure 9:
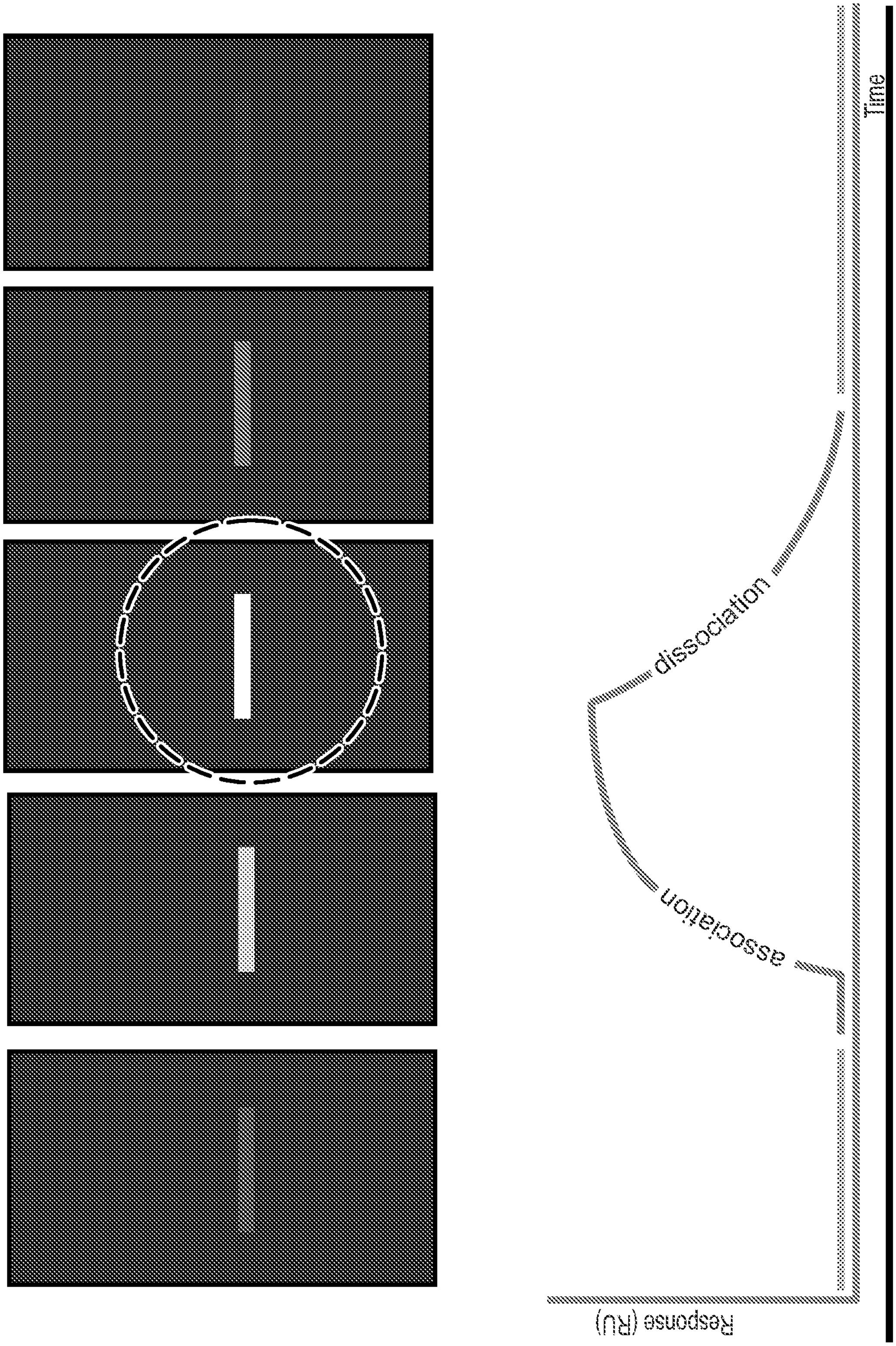
FIG. 9 is a schematic diagram of an example of a Western Blot assay performed according to an embodiment of the present disclosure.

FIG. 9 is a schematic diagram of an example of a Western Blot assay performed according to an embodiment of the present disclosure. Specifically, FIG. 9 illustrates a time-scan detector signal (measured intensity versus time, in arbitrary units), and a membrane at different points in time while the detector signal is being acquired. The horizontal time axis corresponds to the probing time period, from its start to its end. FIG. 9 shows one band of target proteins on the membrane in different states during the probing time period, specifically at five different time points or stages during the probing process.

As shown in the example of FIG. 9, during the initial (leftmost) stage of the probing process, no specific binding events have yet occurred, and accordingly the measured intensity level of the detector signal is at a baseline. During the next (second) stage, specific binding events (association between the probe molecules and target proteins) begin to occur, and accordingly the measured intensity level of the detector signal increases as illustrated. During the next (third) stage, the number of specific binding events reaches a maximum, as indicated by a peak on the detector signal. In the following stages, some of the probe molecules previously bound to the target proteins become unbound (dissociation). Consequently, the measured intensity level of the detector signal decreases eventually back to the base line.

As evident in the example of FIG. 9, the experimental conditions of this particular assay are such that the detector signal is optimized at an intermediate stage of the probing process. The method according to the present disclosure, in which the detector signal is acquired in real time during the probing process, enables this observation to be made. By contrast, the endpoint measurement of the conventional Western Blot assay would not be made until after the end of the probing process, and therefore would not produce the time-varying detection signal illustrated in FIG. 9. Moreover, as evident from the state of the membrane at the last (rightmost) stage of the probing process, the conventional Western Blot assay would not be able to detect the target protein at all due to the dissociation that has already occurred by this endpoint in time. Thus, in this example, the endpoint measurement of the conventional Western Blot assay would result in a false negative.

To produce a time-scan detector signal such as illustrated in FIG. 9, measuring the intensity of the detection signal may be done iteratively (e.g., a plurality of times at a desired frequency of detection) during the probing time period, or (substantially) continuously during the probing time period. In either case, the data points may be collected to generate the time-scan detector signal.

Figure 10:
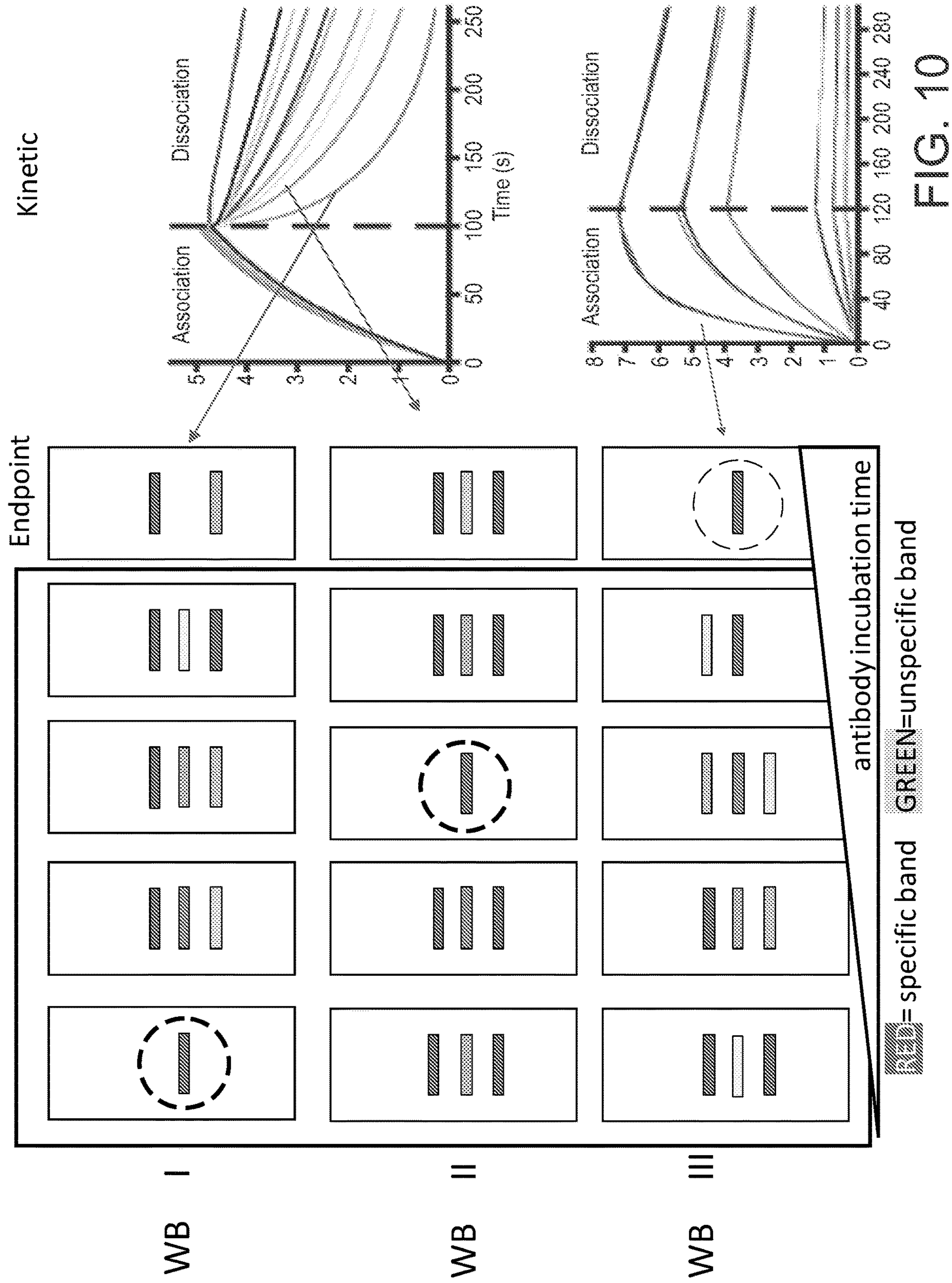
FIG. 10 is a schematic diagram of an example of three different Western Blot assays performed according to an embodiment of the present disclosure.

FIG. 10 is a schematic diagram of an example of three different Western Blot assays (WB I, WB II, and WB III) performed according to an embodiment of the present disclosure. Specifically, for each assay, FIG. 10 illustrates the membrane at five different points in time (stages) along a horizontal time axis, while the probing process is proceeding and (according to the method disclosed herein) while the detector signal is being acquired. On the membrane of each assay, FIG. 10 shows three (vertically) separated bands of proteins, with the middle band being the specific band (containing the target proteins) and the upper and lower bands being unspecific bands (containing non-target proteins). FIG. 10 also includes kinetic time-scan detector signals corresponding to the assays, acquired in accordance with the method disclosed herein.

In the first assay (WB I) of FIG. 10, it is seen that the optimum time for measuring the target proteins occurs during the initial stage of the probing process, after which the detector signal corresponding to detection and measurement of the target proteins falls off due to dissociation, such that the target proteins are not detectable during the last stage. Meanwhile, detectable unspecific binding events begin to occur after the initial stage and remain detectable during the last stage. Therefore, for this assay, the best time to measure the target proteins is during the initial stage, which is enabled by the dynamic, real-time measurement implemented by the method of the present disclosure. By contrast, the conventional Western Blot assay would miss the best result. Moreover, as evident from the state of the membrane at the last (rightmost) stage the endpoint measurement of the conventional Western Blot assay would result in a false negative (no detection of target proteins) and false positives (detection of non-target proteins).

In the second assay (WB II) of FIG. 10, it is seen that the optimum time for measuring the target proteins occurs during an intermediate stage of the probing process, which is observable from the dynamic, real-time measurement made by the method of the present disclosure, and would not be observable from the endpoint measurement made by the conventional Western Blot assay. Here again, the conventional Western Blot assay would miss the best result. Moreover, at the last stage, to which the conventional Western Blot assay is limited, the detector signal is a composite of responses of varying intensity from both target proteins and non-target proteins. Such a composite signal would be difficult to interpret and could lead to inaccurate or incorrect analyses or conclusions regarding the data.

In the third assay (WB III) of FIG. 10, it is seen that the optimum time for measuring the target proteins occurs during the last stage of the probing process, where only the labeled target proteins contribute to the detector signal. In this particular assay, the conventional Western Blot assay may be successful in acquiring good data regarding the target proteins. However, as an endpoint measurement, it is still the case that the conventional Western Blot assay acquires no detector signal during the course of the probing process, and thus is not able to obtain any potentially useful information during the probing process regarding any of the proteins, binding events, interactions, etc.

In some embodiments, the present disclosure provides a multiplex Western Blot assay. In the present context, "multiplexing" refers to measuring a plurality of (two or more) different target proteins contained in the same Western Blot sample simultaneously (or in parallel), and in real time during the probing process as described herein. In a multiplexing embodiment, the FRET solution includes different probe pairs configured to specifically bind to the corresponding different target proteins. The different probe pairs form different donor-acceptor pairs when bound to the corresponding different target proteins. The donor-acceptor pairs are different at least in the sense that the acceptor molecules emit emission light at different wavelengths, thereby allowing different target proteins to be discriminated during measurement.

Multiplexing is useful for measuring two or more different target proteins of interest, for example two or more different biomarkers, in a single Western Blot assay. Multiplexing may also be utilized for normalization of total protein load between different samples, such as to correct or compensate for the effects of any experimental errors occurring during the performance of the Western Blot assay (e.g., in sample preparation, sample loading on the gel support, protein transfer to the membrane, etc.). In this case, one of the target proteins may be a housekeeping protein to which a target protein of interest is normalized. The use of a housekeeping protein for Western Blot normalization is generally understood by persons skilled in the art. Examples of housekeeping proteins (or other molecules) include, but are not limited to, actin, tubulin, and the enzyme glyceraldehyde 3-phosphate dehydrogenase (GAPDH).

In another embodiment, the blotting membrane includes at least two different target proteins of interest, namely a first target protein and a second target protein. The first target protein is an unmodified protein, and the second target protein is a modified version (or variant) of the unmodified protein. In such cases, it may be desirable to calculate the ratio of the modified protein to the unmodified protein based on the measured intensities of first detection signal acquired from the labeled modified protein and a second detection signal acquired from the labeled unmodified protein. As one non-exclusive example, it is often desirable to study phosphorylated proteins, as in many cellular pathways proteins are activated through phosphorylation, which is carried out via catalysis using the kinase enzyme as appreciated by persons skilled in the art. In this case, the modified protein may be a phosphorylated version of the unmodified (non-phosphorylated) protein. If desired, the ratio of the phosphorylated protein to the non-phosphorylated protein may be calculated based on the respective intensities of the detector signals measured.

In an embodiment, the method for performing a multiplex Western Blot assay is similar to the method described above in conjunction with FIG. 6. The different target proteins are positioned in different lanes on the blotting membrane. The FRET solution added to the membrane during the probing process contains multiple chromophores (and associated probe molecules, depending on the embodiment) of the type needed for forming different donor-acceptor pairs when bound to the corresponding different target proteins. Some of the chromophores may already be provided in the sample at the time of adding the FRET solution, as described above. A plurality of light sources configured to generate excitation light at different wavelengths may be utilized as needed for exciting different donor fluorophores of the different donor-acceptor pairs. Alternatively, a single light source configured to generate broadband light (at least spanning the range of excitation wavelengths required for a given assay) may be utilized. As another alternative, multiple light sources (a single light source whose excitation light beam is split into multiple beams) may be utilized in conjunction with different excitation light filters configured to pass different wavelengths of excitation light. Similarly, a plurality of light detectors may be utilized to measure the emission light emitted by the different target proteins. Separate light detectors may be configured to measure different wavelengths of emission light. For example, separate light detectors may be sensitive to emission light propagating at different specific wavelengths. As another example, each light detector may be generally capable of measuring emission light over the same range of wavelengths, but receive differently filtered emission light. That is, different emission light filters configured to pass different wavelengths of emission light may be positioned in the optical paths of the respective light detectors.

Figure 11:
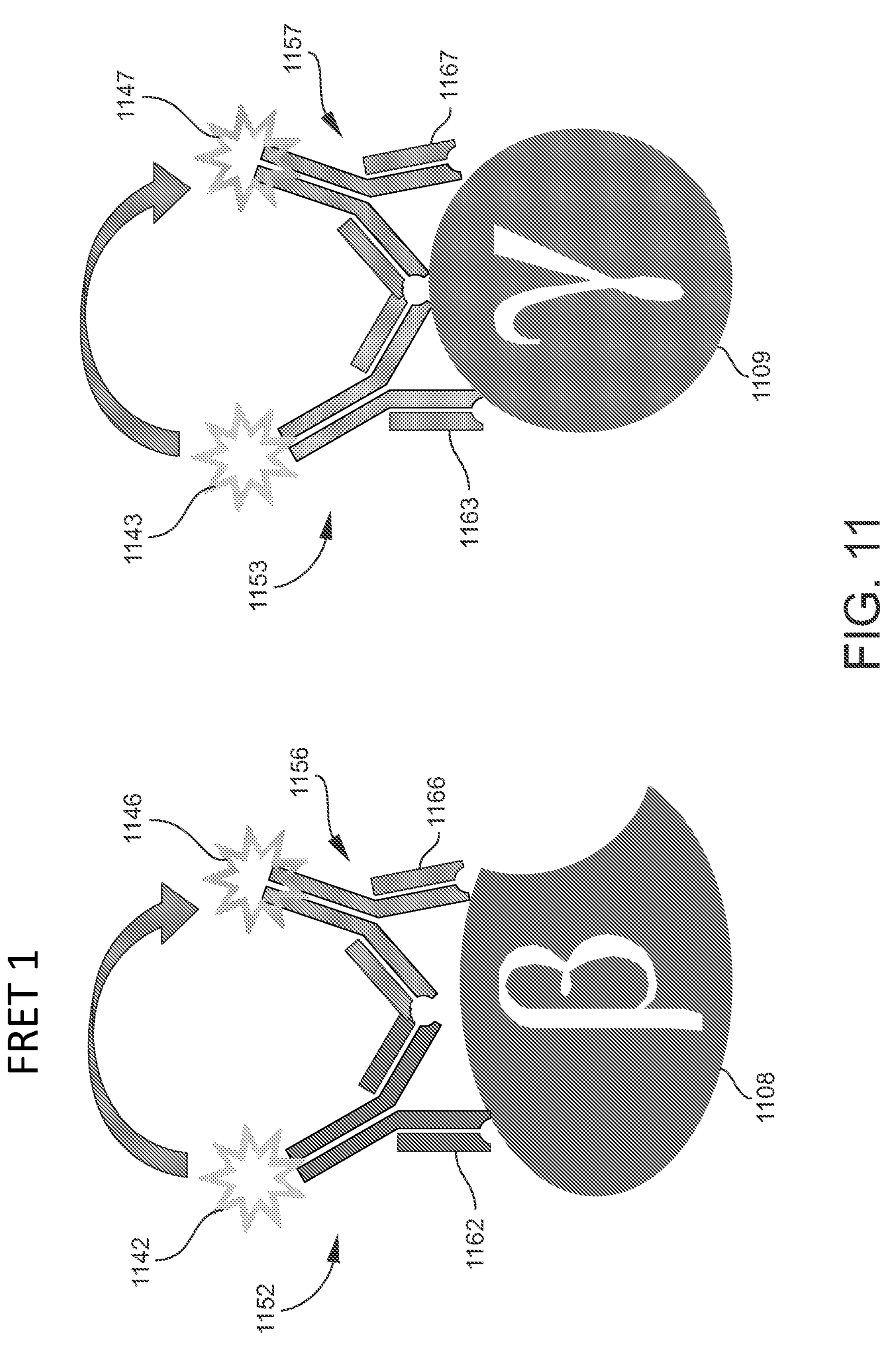
FIG. 11 illustrates a non-exclusive example of a configuration of a labeled first target protein and a labeled second target protein that may be formed as part of a multiplex Western Blot assay, according to an embodiment of the present disclosure.

FIG. 11 illustrates a non-exclusive example of a configuration of a labeled first target protein 1105 and a labeled second target protein 1107 that may be formed as part of a multiplex Western Blot assay, according to an embodiment of the present disclosure. In this embodiment, the first target protein 1105 and the second target protein 1107 are separated in different bands on a blotting membrane. During the probing process, the membrane is contacted with a FRET solution containing a first (donor) probe 1152, a second (acceptor) probe 1156, a third (donor) probe 1153, and a fourth (acceptor) probe 1157.

In the present example, the first probe 1152 includes a first (donor) probe molecule 1162 (e.g., an antibody or other type) and a first (donor) chromophore 1142 attached thereto. The second probe 1156 includes a second (acceptor) probe molecule 1166 and a second (acceptor) chromophore 1146 attached thereto. During the probing process, the first probe molecule 1162 and the second probe molecule 1166 bind to the first target protein 1105, thereby forming a donor-acceptor pair sufficient for FRET to occur between the first chromophore 1142 and the second chromophore 1146 in response to an appropriate excitation.

Also in this example, the third probe 1153 includes a third (donor) probe molecule 1163 and a third (donor) chromophore 1143 attached thereto. The fourth probe 1157 includes a fourth (acceptor) probe molecule 1167 and a fourth (acceptor) chromophore 1147. During the probing process, the third probe molecule 1163 and the fourth probe molecule 1167 bind to the second target protein 1107, thereby forming a donor-acceptor pair sufficient for FRET to occur between the third chromophore 1143 and the fourth chromophore 1147 in response to an appropriate excitation.

The first target protein 1105 and the second target protein 1107 may be measured during the course of the probing process, as in other embodiments. In the present embodiment, the membrane is irradiated with a first excitation light and a second excitation light, which may be done simultaneously. The first excitation light propagates at a first excitation wavelength effective to excite the first (donor) chromophores 1142, and the second excitation light propagates at a second excitation wavelength effective to excite the third (donor) chromophores 1143. Typically, the first chromophores 1142 and the third chromophores 1143 are different, in which case the first excitation wavelength and the second excitation wavelength required are different. In each irradiated labeled first target protein 1105, the excited first chromophore 1142 transfers energy to the second chromophore 1146 by FRET and, in response, the second fluorophore 1146 (if a fluorophore) emits a first emission light. In each irradiated labeled second target protein 1107, the excited third chromophore 1143 transfers energy to the fourth chromophore 1147 by FRET and, in response, the fourth chromophore 1147 (if a fluorophore) emits a second emission light at a wavelength different from the first emission light. The respective intensities of the first emission light and the second emission light are then measured by the light detector(s), which may be done simultaneously.

Other embodiments of target proteins labeled for a multiplex Western Blot assay may encompass configurations similar or analogous to those described above in conjunction with FIGS. 8B to 8D.

Figure 12:
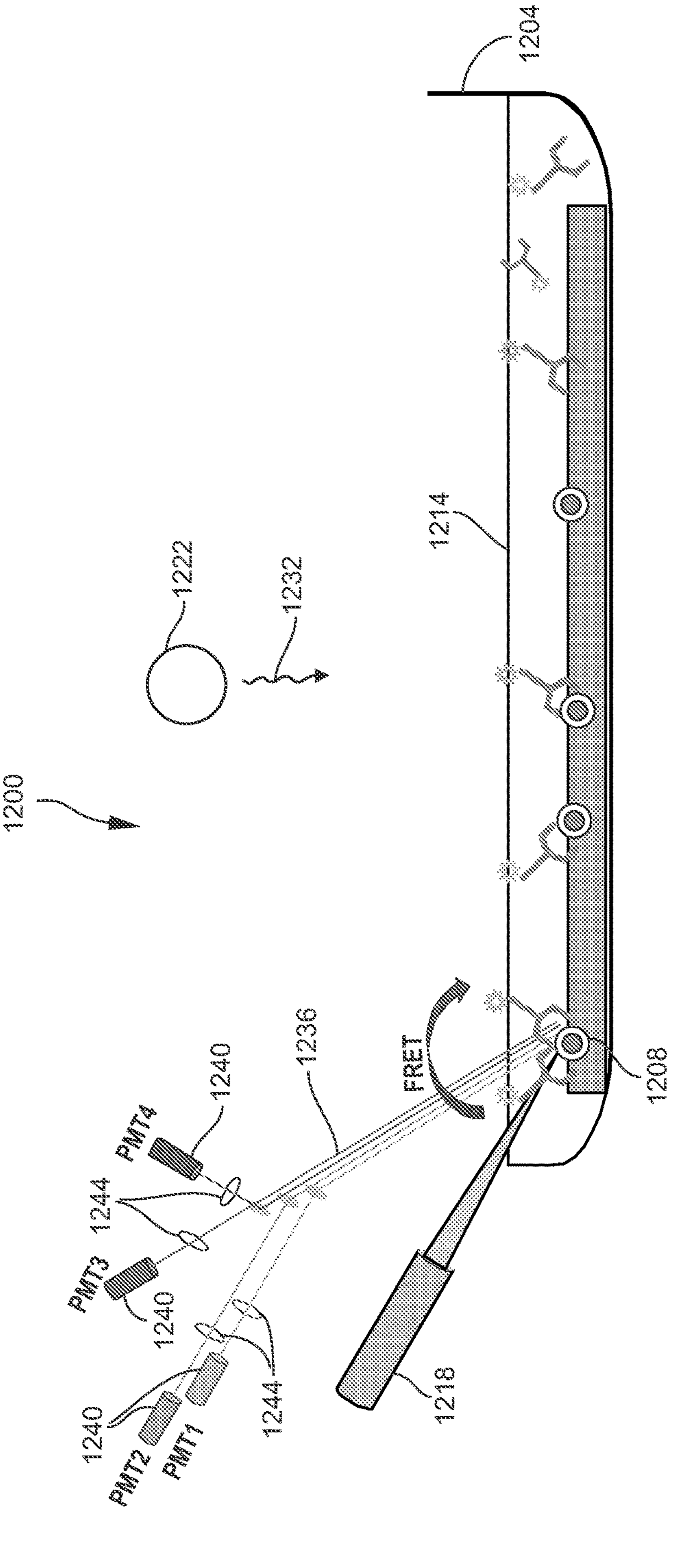
FIG. 12 is a schematic view of an example of a sample analyzing apparatus that may be utilized in the methods disclosed herein.

FIG. 12 is a schematic view of an example of a sample analyzing apparatus 1200 that may be utilized in the methods disclosed herein. Generally, the structure and operation of the various components provided in optical-based sample analysis instruments are understood by persons skilled in the art, and thus are only briefly described herein to facilitate an understanding of the presently disclosed subject matter.

The sample analyzing apparatus 1200 includes a container 1204 configured to support a Western Blot membrane 1212 prepared as described herein. The membrane 1212 thus supports a plurality of proteins, including target proteins 1208 for which a detector signal is to be acquired. The container 1204 is also configured to support a FRET solution 1214 as described herein. In one embodiment, the container 1204 is, or is part of, an enclosed cartridge that is removably mounted to or installed in the sample analyzing apparatus 1200. The FRET solution 1214 may be added to the container 1204 using a suitable dispensing device 1218, such that the membrane 1212 is immersed in (i.e., soaked up and overlayed by) the FRET solution 1214, thereby initiating the probing process. In one embodiment, the dispensing device 1218 is a pipette tip or an injector needle that is part of an automated or semi-automated liquid dispensing system, which may include other components such as tubing, pump(s), reservoir(s), etc., as appreciated by persons skilled in the art.

The sample analyzing apparatus 1200 further includes one or more light sources 1222 configured to generate one or more excitation light beams 1232 at one or more different excitation wavelengths, and direct the light beam(s) to the membrane 1212, as described herein. Depending on the embodiment, the light source(s) 1222 may include a broadband light source (e.g., a Xenon flash lamp) or one or more light emitting diodes (LEDs), laser diodes (LDs), lasers, etc. Appropriate excitation optics (not shown) may be positioned in the optical path(s) between the light source 1222 and the membrane 1212. The excitation optics may include, for example, one or more lenses, apertures, filters, wavelength selectors, light guides, mirrors, beam splitters, beam expanders, optical path switches, etc.

The sample analyzing apparatus 1200 further includes one or more light detectors 1240 configured to receive and measure one or more emission light beams 1236 at one or more different excitation wavelengths, as described herein. The light detector 1240 typically is a photomultiplier tube (PMT), but other types of light detectors may be suitable such as, for example, a photodiode, a charge-coupled device (CCD), an active-pixel sensor (APS) such as a complementary metal-oxide-semiconductor (CMOS) device, etc. Emission filters 1244 and other appropriate emission optics (not shown) may be positioned in the optical path(s) between the membrane 1212 and the light detector(s) 1240. In addition to emission filters 1244, the emission optics may include, for example, one or more lenses, read heads, apertures, filters, wavelength selectors, light guides, mirrors, beam splitters, monochromators, diffraction gratings, prisms, optical path switches, etc. The sample analyzing apparatus 1200 may also include a device for acquiring images of the membrane 1212, such as a camera (not shown).

It will be understood that terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for performing a Western Blot assay, the method comprising:

(a) obtaining a membrane comprising a spatially separated plurality of proteins suspected of comprising one or more target proteins;

(b) performing a probing process comprising contacting the plurality of proteins supported on the membrane with a fluorescent resonance energy transfer (FRET) solution and allowing the probing process to proceed over a probing time period, wherein:

the FRET solution comprises first and second probes, the probing process causing interactions between the first and second probes and the target proteins to produce labeled target proteins, each first and second probes bound to the same target proteins, and wherein the first probes each comprise a first donor chromophore, the second probes each comprise a first acceptor chromophore, and the first donor chromophore and the first acceptor chromophore are a donor-acceptor pair for FRET; and (c) measuring the labeled target proteins while performing the probing process, the measuring comprising irradiating the membrane with an excitation light to excite the donor chromophores, thereby causing the donor chromophores to transfer energy to the acceptor chromophores by FRET such that each of the labeled target proteins emits light; and measuring intensity of the emitted light.

2. The method of claim 1, wherein measuring the intensity of the emission light is initiated simultaneously or substantially simultaneously with contacting the sample with the FRET solution.

3. The method of claim 1, wherein measuring the intensity of the emission light is initiated after a delay period following contacting the sample with the FRET solution.

4. The method of claim 3, wherein the delay period has a duration of 1 second or less.

5. The method of claim 1, comprising generating a time-scan detector signal based on the measured intensity of the emission light over time.

6. The method of claim 1, wherein the probing time period has a duration in a range from 5 minutes to 24 hours.

7. The method of claim 1, wherein measuring the intensity of the emission light is done in a plurality of iterations during the probing time period.

8. The method of claim 1, wherein measuring the intensity of the emission light is done over a continuous measurement period during the probing time period.

9. The method of claim 1, wherein the obtaining a membrane comprises obtaining a sodium dodecyl sulfate polyacrylamide gel (SDS-PAGE) comprising a spatially separated plurality of proteins suspected of comprising one or more target proteins; and transferring the spatially separated plurality of proteins to the membrane.

10. The method of claim 9, wherein the transferring comprises electroblotting onto the membrane.

11. The method of claim 1, wherein the membrane is suitable for immunostaining of the one or more target proteins among the separated proteins, optionally wherein the membrane is a nitrocellulose or polyvinylidene difluoride (PVDF) membrane.

12. The method of claim 9, further comprising providing a sample comprising the plurality of proteins optionally including one or more target proteins; and separating the plurality of proteins comprising electrophoresis to obtain the SDS-PAGE gel comprising the spatially separated proteins.

13. The method of claim 1, wherein performing the probing process and measuring the intensity of the emission light are done without removing unbound first probes and unbound second probes from the sample.

14. The method of claim 1, wherein the acceptor chromophores are fluorophores.

15. The method of claim 14, wherein measuring the intensity of the emission light is selected from the group consisting of: measuring an intensity of emission light emitted by the donor chromophores; measuring an intensity of emission light emitted by the acceptor chromophores; and measuring an intensity of both the donor chromophores and the acceptor chromophores.

16. The method of claim 1, wherein the acceptor chromophores are non-fluorescent quenchers.

17. The method of claim 16, wherein measuring the intensity of the emission light comprises measuring an intensity of emission light emitted by the donor chromophores.

18. The method of claim 1, wherein the donor chromophores and the acceptor chromophores are selected from the group consisting of: fluorescent proteins; fluorescent dyes; lanthanides; transition metals; upconversion phosphors; and quantum dots.

19. The method of claim 1, wherein:

the first probes comprise first probe molecules that bind directly to the target proteins, and the first donor chromophores are attached to the first probe molecules; and the second probes comprise second probe molecules that bind directly to the target proteins, and the first acceptor chromophores are attached to the second probe molecules.

20. The method of claim 1, wherein the first probes comprise first primary probe molecules that bind directly to the target proteins, and the first donor chromophores are attached to the first primary probe molecules; and the second probes comprise second primary probe molecules that bind directly to the target proteins, and secondary probe molecules that bind to the second primary probe molecules, and the first acceptor chromophores are attached to the secondary probe molecules.

21. The method of claim 1, wherein the first probes comprise first primary probe molecules that bind directly to the target proteins, and the first donor chromophores are attached to the first primary probe molecules; and the second probes comprise second primary probe molecules that bind directly to the target proteins, and secondary probe molecules that bind to the second primary probe molecules, and the first acceptor chromophores are attached to the secondary probe molecules.

22. The method of claim 1, wherein the first probes comprise first primary probe molecules that bind directly to the target proteins, and first secondary probe molecules that bind to the first primary probe molecules, and the first donor chromophores are attached to the first secondary probe molecules; and the second probes comprise second primary probe molecules that bind directly to the target proteins, and the first acceptor chromophores are attached to the second primary probe molecules.

23. The method of claim 1, wherein the plurality of target proteins comprises first target proteins and second target proteins different from the first target proteins; and wherein the labeled target proteins of step (c) comprise first labeled target proteins and second labeled target proteins, wherein the second labeled target proteins are produced by interactions between third probes comprising second donor chromophore and fourth probes comprising second acceptor chromophore and the second target proteins, wherein the second donor chromophore and the second acceptor chromophore are a donor-acceptor pair for FRET;

wherein the step of irradiating the membrane comprises irradiating the membrane with a first excitation light to excite the first donor chromophores of the labeled first target proteins and irradiating the membrane with a second excitation light to excite the second donor chromophores of the labeled second target proteins, wherein the labeled second target proteins emit light at a wavelength different from the emitted light of the labeled first target proteins; and wherein measuring intensity of the emitted light comprises measuring intensity of emitted light from the labeled first and second target proteins.

24. The method of claim 23, wherein the third probes, the fourth probes, or both the third probes and the fourth probes are provided in the FRET solution.

25. The method of claim 23, wherein the first target proteins or the second target proteins are housekeeping proteins.

26. The method of claim 23, wherein the first target proteins are unmodified proteins and the second target proteins are modified versions of the unmodified proteins.

27. The method of claim 23, wherein the first target proteins are non-phosphorylated proteins and the second target proteins are phosphorylated proteins.

28. The method of claim 1, wherein at least one of the first probes or the second probes comprise probe molecules selected from the group consisting of: antibodies; antibody fragments or domains; streptavidin; avidin; (poly) peptides; nucleic acids; carbohydrates; lipids; and small molecules.

* * * * *